(12) United States Patent
Seki et al.

(10) Patent No.: US 7,888,014 B2
(45) Date of Patent: Feb. 15, 2011

(54) **METHOD OF DETECTING *HAEMOPHILUS INFLUENZAE* TYPE B, PRIMER SET AND KIT FOR THE USE IN THE METHOD**

(75) Inventors: Mitsuko Seki, Tokyo (JP); Hirotaka Torigoe, Tokyo (JP)

(73) Assignee: Nihon University, Tokyo (JP)

( * ) Notice: Subject to any disclaimer, the term of this patent is extended or adjusted under 35 U.S.C. 154(b) by 428 days.

(21) Appl. No.: 11/665,566

(22) PCT Filed: May 16, 2005

(86) PCT No.: PCT/JP2005/008921

§ 371 (c)(1),
(2), (4) Date: Apr. 17, 2007

(87) PCT Pub. No.: WO2006/043349

PCT Pub. Date: Apr. 27, 2006

(65) Prior Publication Data

US 2008/0305472 A1 Dec. 11, 2008

(30) Foreign Application Priority Data

Oct. 19, 2004 (JP) ............................. 2004-304879

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.3; 536/24.33

(58) Field of Classification Search .............. 435/6, 435/91.2; 536/24.3, 24.33
See application file for complete search history.

(56) References Cited

U.S. PATENT DOCUMENTS 6,410,278 B1 * 6/2002 Notomi et al. ............. 435/91.2
7,175,985 B1 * 2/2007 Kanda et al. .................... 435/6
2003/0207292 A1 * 11/2003 Notomi et al. ................... 435/6

OTHER PUBLICATIONS

Lowe et al., Nucleic Acids Research 18(7), 1757-1761 (1990).*
Nagamine K. et al., Mol. Cell Probes, Jun. 2002, 16(3), pp. 223-229.
Ueyama T. et al., J. Clin. Microbiol., Jul. 1995, 33(7), pp. 1835-1838.
Nelson M.B. Infect Immun., Jan. 1988, 56(1), pp. 128-134.
Falla T.J. et al., J. Clin. Microbial., Oct. 1994, 32(10), pp. 2382-2386.
Van Eldere J. et al., Mol. Microbiol., Jan. 1995, 15(1), pp. 107-118.

* cited by examiner

*Primary Examiner*—Kenneth R. Horlick
(74) *Attorney, Agent, or Firm*—Birch, Stewart, Kolasch & Birch, LLP

(57) ABSTRACT

The present invention provides a method of detecting *Haemophilus influenzae*, which enables accurate and rapid detection of *H. influenzae*, a primer set for detecting *H. influenzae*, and a kit for detecting *H. influenzae*. Nucleic acid amplification is carried out using the DNA of *H. influenzae* as a template, and also using the LAMP primers as shown in SEQ ID NOS: 1 to 5 given as examples of the present invention. Thus, the presence or absence of the amplified product is detected. When primers having sequences that are complementary to the sequences as shown in SEQ ID NOS: 1 to 5 are used, such primers are excellent in terms of detection sensitivity and promptness of detection, as well as specificity. In addition, as another example of the present invention, nucleic acid amplification is carried out using LAMP primers as shown in SEQ ID NOS: 43 to 47, and the presence or absence of the amplified product is detected. Thereby, *H. influenzae* Type b can be distinguished from other capsular serotype and non-encapsulated type *H. influenzae*, and it can be detected rapidly, simply, and accurately.

6 Claims, 23 Drawing Sheets

Fig 8

| Examples (correspondence to claims) | FIP | BIP | F3 | B3 | LP (LF or LB) | Target position | Threshold time |
|---|---|---|---|---|---|---|---|
| Example 1 (claim 3(s)) | SEQ ID NO: 1 | SEQ ID NO: 2 | SEQ ID NO: 3 | SEQ ID NO: 4 | SEQ ID NO: 5 (LF) | 254-458 | 18 min 30 sec |
| Example 2 (claim 3(u)) | SEQ ID NO: 6 | SEQ ID NO: 7 | SEQ ID NO: 8 | SEQ ID NO: 9 | SEQ ID NO: 10 (LF) | 271-450 | 19 min 24 sec |
| Example 3 (claim 2(e)) | SEQ ID NO: 11 | SEQ ID NO: 7 | SEQ ID NO: 8 | SEQ ID NO: 9 | None | 271-450 | 32 min 24 sec |
| Example 4 (claim 3(w)) | SEQ ID NO: 15 | SEQ ID NO: 16 | SEQ ID NO: 17 | SEQ ID NO: 18 | SEQ ID NO: 19 (LB) | 227-400 | 39 min |
| Example 5 (claim 2(q)) | SEQ ID NO: 33 | SEQ ID NO: 34 | SEQ ID NO: 35 | SEQ ID NO: 36 | None | 192-401 | 46 min 42 sec |
| Example 6 (claim 2(k)) | SEQ ID NO: 24 | SEQ ID NO: 25 | SEQ ID NO: 26 | SEQ ID NO: 27 | None | 112-329 | 46 min |
| Example 7 (claim 2(m)) | SEQ ID NO: 28 | SEQ ID NO: 29 | SEQ ID NO: 26 | SEQ ID NO: 30 | None | 112-314 | 44 min 12 sec |
| Example 8 (claim 2(o)) | SEQ ID NO: 31 | SEQ ID NO: 32 | SEQ ID NO: 26 | SEQ ID NO: 30 | None | 112-314 | 43 min 54 sec |
| Example 9 (claim 2(i)) | SEQ ID NO: 20 | SEQ ID NO: 21 | SEQ ID NO: 22 | SEQ ID NO: 23 | None | 93-328 | 43 min |
| Comparative Example 2 | SEQ ID NO: 37 | SEQ ID NO: 38 | SEQ ID NO: 39 | SEQ ID NO: 40 | None | 27-230 | 109 min |
| Comparative Example 3 | SEQ ID NO: 41 | SEQ ID NO: 42 | SEQ ID NO: 39 | SEQ ID NO: 40 | None | 27-230 | 60 min 36 sec |

Fig. 9

| Strain name | Example | | | | | | | | | Comparative example | | |
|---|---|---|---|---|---|---|---|---|---|---|---|---|
| | 1 | 2 | 3 | 4 | 5 | 6 | 7 | 8 | 9 | 1 | 2 | 3 |
| Streptococcus mitis ATCC9811 [a] | − | − | − | − | − | − | − | − | − | − | − | − |
| Streptococcus oralis ATCC10557 [a] | − | − | − | − | − | − | − | − | − | − | − | − |
| Streptococcus gordonii ATCC10558 | − | − | − | − | − | − | − | − | − | − | − | − |
| Streptococcus mutans XC47 | − | − | − | − | − | − | − | − | − | − | − | − |
| Streptococcus sanguis ATCC10556 [a] | − | − | − | − | − | − | − | − | − | − | − | − |
| Streptococcus salivarius HHT [a] | − | − | − | − | − | − | − | − | − | − | − | − |
| Streptococcus pneumoniae ATCC6305 | − | − | − | − | − | − | − | − | − | − | − | − |
| Streptococcus pneumoniae R6 (ATCC BAA-255) | − | − | − | − | − | − | − | − | − | − | − | − |
| Streptococcus pneumoniae GTC261 [b] | − | − | − | − | − | − | − | − | − | − | − | − |
| Streptococcus pneumoniae IID553 [c] | − | − | − | − | − | − | − | − | − | − | − | − |
| Streptococcus pneumoniae IID554 [c] | − | − | − | − | − | − | − | − | − | − | − | − |
| Escherichia coli DH5 | − | − | − | − | − | − | − | − | − | − | − | − |
| Actinobacillus actinomycetemcomitans Y-4 | − | − | − | − | − | − | − | − | − | − | − | − |
| Porhyromonas gingivalis 381 [a] | − | − | − | − | − | − | − | − | − | − | − | − |
| Porhyromonas gingivalis ATCC49417 [a] | − | − | − | − | − | − | − | − | − | − | − | − |
| Actinomyces naeslundii WVU627 [a] | − | − | − | − | − | − | − | − | − | − | − | − |
| Prevotella intermedia ATCC25611 [a] | − | − | − | − | − | − | − | − | − | − | − | − |
| Prevotella nigrescens ATCC25261 [a] | − | − | − | − | − | − | − | − | − | − | − | − |
| Haemophilus influenzae Rd serotype d | + | + | + | + | + | + | + | + | + | + | − | + |
| Haemophilus influenzae IID983 [c] serotype a | + | + | + | + | + | + | + | + | + | + | − | + |
| Haemophilus influenzae IID984 [c] serotype b | + | + | + | + | + | + | + | + | + | + | − | + |
| Haemophilus influenzae IID985 [c] serotype c | + | + | + | + | + | + | + | + | + | + | − | + |
| Haemophilus influenzae IID986 [c] serotype d | + | + | + | + | + | + | + | + | + | + | − | + |
| Haemophilus influenzae IID987 [c] serotype e | + | + | + | + | + | + | + | + | + | + | − | + |
| Haemophilus influenzae IID988 [c] serotype f | + | + | + | + | + | + | + | + | + | + | − | + |
| Haemophilus influenzae IID989 [c] nontype | + | + | + | + | + | + | + | + | + | + | − | + |
| Haemophilus influenzae biotype aegyptius IID993 [c] | + | + | + | + | + | + | + | + | + | + | − | + |
| Haemophilus parainfluenzae IID991 [c] | − | − | − | − | − | − | − | − | − | + | − | − |

Fig. 10

|  | Template DNA concentration (copy number) | | | | | | | |
|---|---|---|---|---|---|---|---|---|
|  | $10^6$ | $10^5$ | $10^4$ | $10^3$ | $10^2$ | 10 | 1 | 0 |
| Example 1 (35 min) | + | + | + | + | − | − | − | − |
| Example 1 (60 min) | + | + | + | + | + | − | − | − |
| Example 2 (35 min) | + | + | + | + | − | − | − | − |
| Example 2 (60 min) | + | + | + | + | + | − | − | − |
| Example 4 (35 min) | − | − | − | − | − | − | − | − |
| Example 4 (60 min) | + | + | + | + | − | − | − | − |
| Example 6 (35 min) | − | − | − | − | − | − | − | − |
| Example 6 (60 min) | + | + | + | + | − | − | − | − |
| Example 7 (35 min) | − | − | − | − | − | − | − | − |
| Example 7 (60 min) | + | + | + | − | − | − | − | − |
| Example 8 (35 min) | − | − | − | − | − | − | − | − |
| Example 8 (60 min) | + | + | + | − | − | − | − | − |
| Example 9 (35 min) | − | − | − | − | − | − | − | − |
| Example 9 (60 min) | + | + | + | + | − | − | − | − |
| Comparative example 1 (PCR) | + | + | + | + | − | − | − | − |
| Comparative example 2 (35 min) | − | − | − | − | − | − | − | − |
| Comparative example 2 (60 min) | − | − | − | − | − | − | − | − |
| Comparative example 3 (35 min) | − | − | − | − | − | − | − | − |
| Comparative example 3 (60 min) | − | − | − | − | − | − | − | − |

Fig. 11

| Species name | | Example 1 | Comparative example 1 |
|---|---|---|---|
| *Haemophilus influenzae* | No. 1 | + | + |
| | No. 2 | + | + |
| | No. 3 | + | + |
| *Haemophilus parainfluenzae* | No. 1 | − | + |
| | No. 2 | − | − |
| | No. 3 | − | + |
| | No. 4 | − | + |
| *Haemophilus parahaemolyticus* | No. 1 | − | + |
| | No. 2 | − | + |

Fig. 12

| No. | 5410 | 5420 | 5430 | 5440 | 5450 | 5460 |
|---|---|---|---|---|---|---|
| Base | tggtacgcca | atacattcaa | caagaaatta | atccaaaaga | aaaatttgcg | tttgttgaat |
| Primer | |——————F3——————> | | | | |——————F2—— |

| No. | 5470 | 5480 | 5490 | 5500 | 5510 | 5520 |
|---|---|---|---|---|---|---|
| Base | tctgggggcg | aggctataca | caagatacct | ttggtcgtct | gctaaatgat | gcctttggta |
| Primer | ——> | |——————LF——————> | <——————F1—— | | | |

| No. | 5530 | 5540 | 5550 | 5560 | 5570 | 5580 |
|---|---|---|---|---|---|---|
| Base | aagaagtaaa | aaacccattc | tattatgtca | gaagttttac | tgatgatatg | ggtacatctg |
| Primer | ————| | | | |——————B1—— | |

| No. | 5590 | 5600 | 5610 | 5620 | 5630 | 5640 |
|---|---|---|---|---|---|---|
| Base | ttcgccataa | cttcatctta | gcaccacaaa | acttctcatt | cttcgagcct | atttttgcac |
| Primer | ——> | <——————B2——————| | | <—— | |

| No. | 5650 | 5660 | 5670 | 5680 | 5690 | 5700 |
|---|---|---|---|---|---|---|
| Base | aaacccata | cgacagtatt | cctgattact | acgaagaaaa | aggcagaatt | gaaccaatta |
| Primer | ——B3———| | | | | | |

| No. | 5710 | 5720 | 5730 | 5740 | 5750 | 5760 |
|---|---|---|---|---|---|---|
| Base | ttaatcaccg | agatagaagc | gtaagcgatc | tcatttcgga | agggttatta | aaatttacag |

| No. | 5770 | 5780 | 5790 | 5800 |
|---|---|---|---|---|
| Base | aagattactt | agcactcaat | acgcaagacg | aagattactt |

Fig. 14

| Examples (correspondence to claims) | FIP | BIP | F3 | B3 | LP (LF or LB) | Target position | Threshold time |
|---|---|---|---|---|---|---|---|
| Example 11 (claim 7(S)) | SEQ ID NO:43 | SEQ ID NO:44 | SEQ ID NO:45 | SEQ ID NO:46 | SEQ ID NO:47 (LF) | 5406-5652 | 16 min 24 sec |
| Example 12 (claim 7(U)) | SEQ ID NO:48 | SEQ ID NO:49 | SEQ ID NO:50 | SEQ ID NO:51 | SEQ ID NO:52 (LB) | 5496-5690 | 38 min |
| Example 13 (claim 7(W)) | SEQ ID NO:53 | SEQ ID NO:54 | SEQ ID NO:55 | SEQ ID NO:56 | SEQ ID NO:57 (LB) | 5571-5748 | 40 min 12 sec |
| Example 14 (claim 6(G)) | SEQ ID NO:58 | SEQ ID NO:59 | SEQ ID NO:60 | SEQ ID NO:61 | None | 1557-1795 | 40 min 54 sec |
| Example 15 (claim 7(Y)) | SEQ ID NO:62 | SEQ ID NO:63 | SEQ ID NO:64 | SEQ ID NO:65 | SEQ ID NO:66 (LB) | 2230-2456 | 31 min |
| Example 16 (claim 6(K)) | SEQ ID NO:67 | SEQ ID NO:68 | SEQ ID NO:69 | SEQ ID NO:70 | None | 2328-2549 | 32 min 6 sec |
| Example 17 (claim 6(M)) | SEQ ID NO:71 | SEQ ID NO:72 | SEQ ID NO:73 | SEQ ID NO:74 | None | 4550-4774 | 24 min 12 sec |
| Example 18 (claim 6(O)) | SEQ ID NO:75 | SEQ ID NO:76 | SEQ ID NO:73 | SEQ ID NO:74 | None | 4550-4774 | 22 min 42 sec |
| Example 19 (claim 6(Q)) | SEQ ID NO:77 | SEQ ID NO:78 | SEQ ID NO:73 | SEQ ID NO:74 | None | 4550-4774 | 25 min |

Fig. 15

| Species name | Strain name | Capsular serotype[a] | Sero-typing[b] | Example 11 | 12 | 13 | 14 | 15 | 16 | 17 | 18 | 19 |
|---|---|---|---|---|---|---|---|---|---|---|---|---|
| H. influenzae | IID983[c] | a | − | − | − | − | − | − | − | − | − | − |
| | IID984[c] | b | + | + | + | + | + | + | + | + | + | + |
| | IID985[c] | c | − | − | − | − | − | − | − | − | − | − |
| | IID986[c] | d | − | − | − | − | − | − | − | − | − | − |
| | IID987[c] | e | − | − | − | − | − | − | − | − | − | − |
| | IID988[c] | f | − | − | − | − | − | − | − | − | − | − |
| | IID989[c] | nt | − | − | − | − | − | − | − | − | − | − |
| H. influenzae (clinically isolated from sample collected from nasopharynx) | CI-1 | b | + | + | + | + | + | + | + | + | + | + |
| | CI-2 | b | + | + | + | + | + | + | + | + | + | + |
| | CI-3 | b | + | + | + | + | + | + | + | + | + | + |
| | CI-4 | b | + | + | + | + | + | + | + | + | + | + |
| | CI-5 | b | + | + | + | + | + | + | + | + | + | + |
| | CI-6 | b | + | + | + | + | + | + | + | + | + | + |
| | CI-7 | b | + | + | + | + | + | + | + | + | + | + |
| | CI-8 | b | + | + | + | + | + | + | + | + | + | + |
| | CI-9 | b | − | + | + | + | + | + | + | + | + | + |
| | CI-10 | nt | − | − | − | − | − | − | − | − | − | − |
| | CI-11 | nt | − | − | − | − | − | − | − | − | − | − |
| | CI-12 | nt | − | − | − | − | − | − | − | − | − | − |
| | CI-13 | nt | − | − | − | − | − | − | − | − | − | − |
| | CI-14 | nt | − | − | − | − | − | − | − | − | − | − |
| | CI-15 | nt | − | − | − | − | − | − | − | − | − | − |
| | CI-16 | nt | − | − | − | − | − | − | − | − | − | − |
| | CI-17 | nt | − | − | − | − | − | − | − | − | − | − |
| | CI-18 | nt | − | − | − | − | − | − | − | − | − | − |
| | CI-19 | nt | − | − | − | − | − | − | − | − | − | − |
| | CI-20 | nt | − | − | − | − | − | − | − | − | − | − |
| | CI-21 | nt | − | − | − | − | − | − | − | − | − | − |
| | CI-22 | nt | − | − | − | − | − | − | − | − | − | − |
| | CI-23 | nt | − | − | − | − | − | − | − | − | − | − |
| | CI-24 | nt | − | − | − | − | − | − | − | − | − | − |
| | CI-25 | nt | − | − | − | − | − | − | − | − | − | − |
| | CI-26 | nt | − | − | − | − | − | − | − | − | − | − |

Fig. 16

| Species name | Example | | | | | | | | |
|---|---|---|---|---|---|---|---|---|---|
| | 11 | 12 | 13 | 14 | 15 | 16 | 17 | 18 | 19 |
| *Streptococcus mitis* ATCC9811[a] | − | − | − | − | − | − | − | − | − |
| *Streptococcus oralis* ATCC10557[a] | − | − | − | − | − | − | − | − | − |
| *Streptococcus gordonii* ATCC10558 | − | − | − | − | − | − | − | − | − |
| *Streptococcus mutans* XC47 | − | − | − | − | − | − | − | − | − |
| *Streptococcus sanguis* ATCC10556[a] | − | − | − | − | − | − | − | − | − |
| *Streptococcus salivarius* HHT[a] | − | − | − | − | − | − | − | − | − |
| *Streptococcus pneumoniae* ATCC6305 | − | − | − | − | − | − | − | − | − |
| *Streptococcus pneumoniae* R6 | − | − | − | − | − | − | − | − | − |
| *Streptococcus pneumoniae* GTC261[b] | − | − | − | − | − | − | − | − | − |
| *Streptococcus pneumoniae* IID553[c] | − | − | − | − | − | − | − | − | − |
| *Streptococcus pneumoniae* IID554[c] | − | − | − | − | − | − | − | − | − |
| *Escherichia coli* DH5. | − | − | − | − | − | − | − | − | − |
| *Actinobacillus actinomycetemcomitans* Y-4 | − | − | − | − | − | − | − | − | − |
| *Porphyromonas gingivalis* 381[a] | − | − | − | − | − | − | − | − | − |
| *Porphyromonas gingivalis* ATCC49417[a] | − | − | − | − | − | − | − | − | − |
| *Actinomyces naeslundii* WVU627[a] | − | − | − | − | − | − | − | − | − |
| *Prevotella intermedia* ATCC25611[a] | − | − | − | − | − | − | − | − | − |
| *Prevotella nigrescens* ATCC25261[a] | − | − | − | − | − | − | − | − | − |
| *Haemophilus parainfluenzae* IID991[c] | − | − | − | − | − | − | − | − | − |
| *Haemophilus parahaemolyticus* GTC1529[b] | − | − | − | − | − | − | − | − | − |
| *Haemophilus aegyptius* IID993[c] | − | − | − | − | − | − | − | − | − |

Fig. 18

|  | Template DNA concentration (copy number) | | | | | | | |
|---|---|---|---|---|---|---|---|---|
|  | $10^6$ | $10^5$ | $10^4$ | $10^3$ | $10^2$ | 10 | 1 | 0 |
| Example 11 (35 min) | + | + | + | + | + | + | + | − |
| Example 11 (60 min) | + | + | + | + | + | + | + | − |
| Example 14 (35 min) | − | − | − | − | − | − | − | − |
| Example 14 (60 min) | + | + | + | + | − | − | − | − |
| Example 15 (35 min) | + | − | − | − | − | − | − | − |
| Example 15 (60 min) | + | + | + | − | − | − | − | − |
| Example 16 (35 min) | + | − | − | − | − | − | − | − |
| Example 16 (60 min) | + | + | + | + | + | − | − | − |
| Example 17 (35 min) | + | + | + | − | − | − | − | − |
| Example 17 (60 min) | + | + | + | + | + | − | − | − |
| Example 18 (35 min) | + | + | − | − | − | − | − | − |
| Example 18 (60 min) | + | + | + | + | + | − | − | − |
| Example 19 (35 min) | + | + | − | − | − | − | − | − |
| Example 19 (60 min) | + | + | + | + | − | − | − | − |
| Comparative example 11 (PCR) | + | + | + | − | − | − | − | − |

Fig. 23
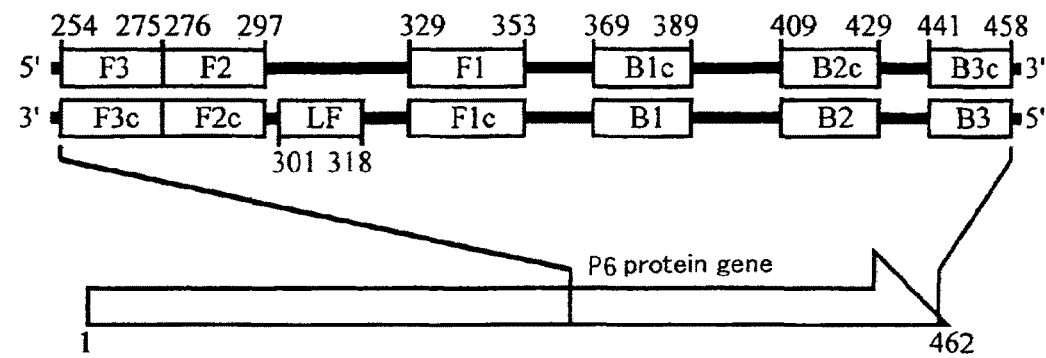
(A)
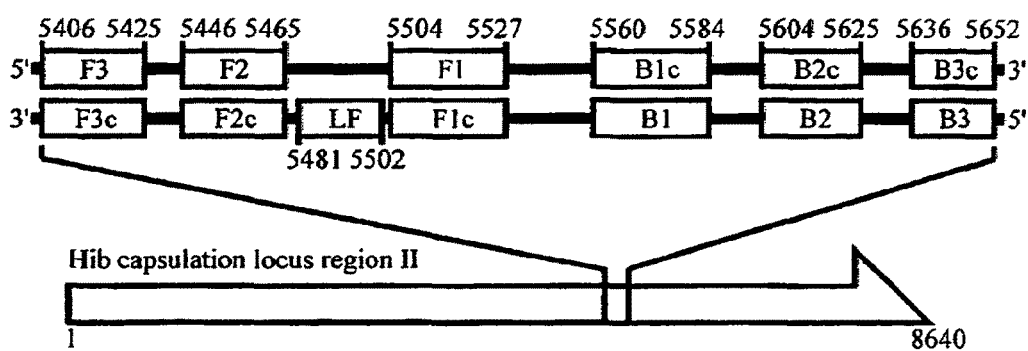
(B)

METHOD OF DETECTING *HAEMOPHILUS INFLUENZAE* TYPE B, PRIMER SET AND KIT FOR THE USE IN THE METHOD

FIELD OF THE INVENTION

The present invention relates to a method of detecting *Haemophilus influenzae*. The present invention particularly relates to a method of detecting *Haemophilus influenzae*, a primer set for detecting *Haemophilus influenzae*, and a kit for detecting *Haemophilus influenzae*.

BACKGROUND OF THE INVENTION

*Haemophilus influenzae* (hereinafter, the term "*Haemophilus*" may also be abbreviated as "*H.*" at times) is a causative bacterium of otitis media, pneumonia, meningitis, and bacteremia. In recent years, appearance of various resistant microbes has become a problem.

In order to detect such *H. influenzae*, selection via culture and a biochemical test have conventionally been used in combination. However, when selection via culture and a biochemical test are used in combination, it takes 3 or more days until infection is determined. In addition, skilled techniques are necessary for precisely selecting its colony based on its form, a difference in color, and the like. Thus, without such skilled techniques, there has been a fear of interfering with clinical diagnosis and the subsequent treatments.

On the other hand, as described in Patent Document 1, detection methods using the PCR (polymerase chain reaction) method have also been adopted in recent years.

In the case of detection in which the PCR method is used, it is common to carry out an amplification reaction using a gene characteristic of *H. influenzae* as a target. As such a gene characteristic of *H. influenzae*, a P6 protein gene encoding a P6 protein that is a surface protein has been known, for example. However, even when such a P6 protein gene has been targeted, it has still been difficult to distinguish *H. influenzae* from *Haemophilus parainfluenzae* (hereinafter abbreviated as "*H. parainfluenzae*" at times), which lives together with *H. influenzae* in the same environment and which is genetically similar thereto. Moreover, in this case, it is possible to enhance specificity by using the hybridization method in combination with the PCR method (Reference 1: T. Ueyama & four other people, "High Incidence of *Haemophilus influenzae* in Nasopharylgeal Secretions and Middle Ear Effusions as Detected by PCR, Journal of Clinical Microbiology," 1995, July, pp. 1835-1838). However, it requires much time and high expenses for detection.

Furthermore, *H. influenzae* is classified into capsular serotypes a to f and non-encapsulated type, in terms of a difference in capsule. Of these, *H. influenzae* Type b (hereinafter abbreviated as "Hib" at times) is a pathogen causing serious diseases such as meningitis, epiglottitis, bacteremia, or pneumonia, particularly in children. Thus, Hib vaccine is inoculated into children in advanced countries other than Japan. However, it has been reported that Hib infection is developed after vaccination. Not only for the original purpose of discovering infection at an early stage, but also for the purpose of confirming the effect of vaccination, a Hib detection method, which is simple and excellent in terms of sensitivity, has been desired. Further, it has also been reported that Hib infection is possibly expanded in developing countries, wherein Hib vaccination has not yet been carried out. Hence, in such countries also, a Hib detection method, which is simply and rapidly carried out, is desired.

However, since phenotypic expression that is characteristic of Hib may be suppressed depending on the type of Hib, the conventional serological typing method has a risk of incorrectly diagnosing infection as negative, or of incorrectly diagnosing non-infection as positive. Thus, the conventional method provides only ambiguous results. In addition, as described in Non-Patent Document 1, there is a detection method that is based on the PCR method, but this method requires much expense in cost, effort, and time, and also requires special equipment such as a thermal cycler. Accordingly, this method has not been easily carried out in a poorly-equipped examination room in a hospital or in the aforementioned developing countries.

The present invention has been made to solve the aforementioned problems. The present invention provides a method of detecting *H. influenzae*, which enables accurate and rapid detection of *H. influenzae* and Hib, a primer set for detecting *H. influenzae*, and a kit for detecting *H. influenzae*.

[Patent Document 1] Japanese Patent Application Laid-Open No. 2000-342268

[Non-Patent Document 1]Falla, T. J., D. W. Crook, L. N. Brophy, D. Maskell, J. S. Kroll, and E. R. Moxon, 1994, PCR for capsular typing of *Haemophilus influenzae*, J. Clin. Microbiol., 32: 2382-2386

DISCLOSURE OF THE INVENTION

In order to achieve the aforementioned object, the present inventors have focused on the LAMP (Loop-mediated isothermal amplification) method, which is more excellent than an amplification reaction via the conventional PCR method, in terms of specificity. At the same time, the present inventors have incorporated a partial region of a P6 protein gene sequence characteristic of *H. influenzae*, which further differs from the sequence of *H. parainfluenzae*, into the sequence of a LAMP primer used in nucleic acid amplification according to the LAMP method, so that the inventors have successfully developed a method of detecting *H. influenzae* having excellent specificity also to *H. parainfluenzae* and other bacteria.

That is to say, the method of detecting *H. influenzae* of the present invention is a method of detecting *H. influenzae* based on the presence or absence of nucleic acid amplification as a result of a nucleic acid amplification reaction using a LAMP primer set, which is characterized in that a LAMP primer set is used as the above-described primer set, wherein all primers have a nucleotide sequence that is identical to or complementary to a partial nucleotide sequence in a nucleotide region located downstream of bp 90 of the P6 protein gene of *H. influenzae*, and wherein at least one primer has a nucleotide sequence that is identical to or complementary to a partial nucleotide sequence in the nonhomologous region ranging from bp 90 to 183, or from bp 337 to 462 of the P6 protein gene of *H. influenzae*.

The nucleotide sequence of the P6 protein gene of *H. influenzae* Rd (GenBank Accession No. NC_000907) is shown in SEQ ID NO: 12 in the sequence listing.

Herein, the primer setting range is determined to be a nucleotide region located downstream of bp 90 of the P6 protein gene. This is because the region ranging from bp 1 to 90 has a low content of GC with a strong hydrogen bond and thus because it is poor in terms of the reaction stability of the primer. Hence, the above region is poor in terms of detection reliability, such that although *H. influenzae* is present, it cannot be detected. Thus, the above region ranging from bp 1 to 90 is not suitable as a primer used in detection. In the nucleotide region located downstream of bp 90, a region that is closer to the 3' end side is preferable.

In addition, in the above-described primer set, all primers have a nucleotide sequence that is identical to or substantially identical to a partial nucleotide sequence in a nucleotide region located downstream of bp 90 of the P6 protein gene of *H. influenzae*, or a nucleotide sequence complementary thereto, and have a nucleotide sequence that is identical to or substantially identical to a partial nucleotide sequence in the nonhomologous region ranging from bp 90 to 183, or from bp 337 to 462 of the P6 protein gene of *H. influenzae*, or a nucleotide sequence complementary thereto. This is because the above-defined region is characteristic of *H. influenzae*, and in particular, it is a region specific to *H. influenzae*, when compared with *H. parainfluenzae*. As stated above, in the above region, a region that is closer to the 3' end side has a high content of GC. Thus, it is preferable to use a LAMP primer set, which comprises a primer having a nucleotide sequence identical to or complementary to a partial nucleotide sequence in the nonhomologous region ranging from bp 337 to 462.

The method of detecting *H. influenzae* of the present invention is characterized in that the above-described LAMP primer set is any one of LAMP primer sets comprising the primers as described in the following (a) to (r):

(a) 4 types of primers each having a nucleotide sequence that is identical to or substantially identical to each of the nucleotide sequences as shown in SEQ ID NOS: 1 to 4 in the sequence listing;

(b) 4 types of primers each having a nucleotide sequence that is complementary to each of the nucleotide sequences as described in (a) above;

(c) 4 types of primers each having a nucleotide sequence that is identical to or substantially identical to each of the nucleotide sequences as shown in SEQ ID NOS: 6 to 9;

(d) 4 types of primers each having a nucleotide sequence that is complementary to each of the nucleotide sequences as described in (c) above;

(e) 4 types of primers each having a nucleotide sequence that is identical to or substantially identical to each of the nucleotide sequences as shown in SEQ ID NOS: 7 to 9 and 11;

(f) 4 types of primers each having a nucleotide sequence that is complementary to each of the nucleotide sequences as described in (e) above;

(g) 4 types of primers each having a nucleotide sequence that is identical to or substantially identical to each of the nucleotide sequences as shown in SEQ ID NOS: 15 to 18;

(h) 4 types of primers each having a nucleotide sequence that is complementary to each of the nucleotide sequences as described in (g) above;

(i) 4 types of primers each having a nucleotide sequence that is identical to or substantially identical to each of the nucleotide sequences as shown in SEQ ID NOS: 20 to 23;

(j) 4 types of primers each having a nucleotide sequence that is complementary to each of the nucleotide sequences as described in (i) above;

(k) 4 types of primers each having a nucleotide sequence that is identical to or substantially identical to each of the nucleotide sequences as shown in SEQ ID NOS: 24 to 27;

(l) 4 types of primers each having a nucleotide sequence that is complementary to each of the nucleotide sequences as described in (k) above;

(m) 4 types of primers each having a nucleotide sequence that is identical to or substantially identical to each of the nucleotide sequences as shown in SEQ ID NOS: 26 and 28 to 30;

(n) 4 types of primers each having a nucleotide sequence that is complementary to each of the nucleotide sequences as described in (m) above;

(o) 4 types of primers each having a nucleotide sequence that is identical to or substantially identical to each of the nucleotide sequences as shown in SEQ ID NOS: 26 and 30 to 32;

(p) 4 types of primers each having a nucleotide sequence that is complementary to each of the nucleotide sequences as described in (o) above;

(q) 4 types of primers each having a nucleotide sequence that is identical to or substantially identical to each of the nucleotide sequences as shown in SEQ ID NOS: 33 to 36; and (r) 4 types of primers each having a nucleotide sequence that is complementary to each of the nucleotide sequences as described in (q) above.

The "primer having a nucleotide sequence that is substantially identical to the nucleotide sequence as shown in the aforementioned sequence number" is used herein to mean a primer, which exhibits almost the same action effects as those of the above primer having the nucleotide sequence as shown in the above-predetermined sequence number, when it is subjected to almost the same reaction as that for the above primer. Examples of such a primer may include primers, wherein the positions in the P6 protein gene, which correspond to regions constituting the LAMP primer, such as F3, F2, F1, B1c, B2c, and B3c, are changed as follows, when compared with regions constituting the LAMP primer having the nucleotide sequence as shown in the above-predetermined sequence number:

1) a primer, wherein the position of the above region, which corresponds to the position in the P6 protein gene, shifts by 1 or 2 nucleotides (for example, the relationship between the region ranging from bp 254 to 275 in the P6 protein gene and the region ranging from bp 255 to 276 in the above primer);

2) a primer, wherein the position of either one of the 5' end and 3' end of the above region, which corresponds to the position in the P6 protein gene, expands or contracts by 1 to 2 nucleotides (for example, the relationship between the region ranging from bp 254 to 275 in the P6 protein gene and the region ranging from bp 255 to 275 in the above primer);

3) a primer, wherein the positions of both of the 5' end and 3' end of the above region, which correspond to the positions in the P6 protein gene, expand by one nucleotide towards each of different directions (for example, the relationship between the region ranging from bp 255 to 275 in the P6 protein gene and the region ranging from bp 254 to 276 in the above primer), or contract by one nucleotide from each of different directions (for example, the relationship between the region ranging from bp 255 to 275 in the P6 protein gene and the region ranging from bp 256 to 274 in the above primer); and 4) a primer, wherein 1 or 2 nucleotides in the above region are substituted with nucleotides different from those in the P6 protein gene, or 1 or 2 nucleotides are deleted.

The aforementioned LAMP primer set is excellent in terms of specificity and detection sensitivity.

The above-described LAMP primer set is characterized in that it is any one of LAMP primer sets comprising the primers as described in the following (s) to (x):

(s) the 4 types of primers according to claim 2(a), and a primer having a nucleotide sequence that is identical to or substantially identical to the nucleotide sequence as shown in SEQ ID NO: 5 in the sequence listing;

(t) the 4 types of primers according to claim 2(b), and a primer having a nucleotide sequence that is identical to or substantially identical to a nucleotide sequence complementary to the nucleotide sequence as shown in SEQ ID NO: 5 in the sequence listing;

(u) the 4 types of primers according to claim 2(c), and a primer having a nucleotide sequence that is identical to or substantially identical to the nucleotide sequence as shown in SEQ ID NO: 10 in the sequence listing;

(v) the 4 types of primers according to claim 2(d), and a primer having a nucleotide sequence that is identical to or substantially identical to a nucleotide sequence complementary to the nucleotide sequence as shown in SEQ ID NO: 10 in the sequence listing;

(w) the 4 types of primers according to claim 2(g), and a primer having a nucleotide sequence that is identical to or substantially identical to the nucleotide sequence as shown in SEQ ID NO: 19 in the sequence listing; and (x) the 4 types of primers according to claim 2(h), and a primer having a nucleotide sequence that is identical to or substantially identical to a nucleotide sequence complementary to the nucleotide sequence as shown in SEQ ID NO: 19 in the sequence listing.

The primers having nucleotide sequences that are identical to or complementary to the nucleotide sequences as shown in SEQ ID NOS: 5, 10, and 19, are so-called Loop primers. Using such primers, the amplification reaction rate becomes faster, and thus, *H. influenzae* can be rapidly detected.

The method of detecting *H. influenzae* of the present invention is a method of detecting Hib based on the presence or absence of nucleic acid amplification as a result of a nucleic acid amplification reaction using a primer set, which is characterized in that a LAMP primer set is used as the above-described primer set, wherein all primers have a nucleotide sequence that is identical to or complementary to a partial nucleotide sequence in the region ranging from bp 1 to 6653 of the capsulation locus region II of the Hib.

Thus, by targeting the capsulation locus region II that is characteristic of Hib, Hib can be distinguished from other capsular serotype and non-encapsulated type *H. influenzae*, and it can be detected. In this case, if the region located after bp 6654 is targeted, since the GC content of the above region is low (approximately 25%), it is difficult to obtain LAMP primers, which are specific to Hib and enable a stable reaction.

Among the methods of detecting *H. influenzae* of the present invention, the method of detecting Hib b is characterized in that a LAMP primer set is used as the above-described LAMP primer set, wherein all primers have a nucleotide sequence that is identical to or complementary to a partial nucleotide sequence in the region ranging from bp 5,000 to 6,653 of the above-described capsulation locus region II.

Among the methods of detecting *H. influenzae* of the present invention, the method of detecting Hib is characterized in that the above-described LAMP primer set is any one of LAMP primer sets comprising the primers as described in the following (A) to (R):

(A) 4 types of primers each having a nucleotide sequence that is identical to or substantially identical to each of the nucleotide sequences as shown in SEQ ID NOS: 43 to 46 in the sequence listing;

(B) 4 types of primers each having a nucleotide sequence that is complementary to each of the nucleotide sequences as described in (A) above;

(C) 4 types of primers each having a nucleotide sequence that is identical to or substantially identical to each of the nucleotide sequences as shown in SEQ ID NOS: 48 to 51;

(D) 4 types of primers each having a nucleotide sequence that is complementary to each of the nucleotide sequences as described in (C) above;

(E) 4 types of primers each having a nucleotide sequence that is identical to or substantially identical to each of the nucleotide sequences as shown in SEQ ID NOS: 53 to 56;

(F) 4 types of primers each having a nucleotide sequence that is complementary to each of the nucleotide sequences as described in (E) above;

(G) 4 types of primers each having a nucleotide sequence that is identical to or substantially identical to each of the nucleotide sequences as shown in SEQ ID NOS: 58 to 61;

(H) 4 types of primers each having a nucleotide sequence that is complementary to each of the nucleotide sequences as described in (G) above;

(I) 4 types of primers each having a nucleotide sequence that is identical to or substantially identical to each of the nucleotide sequences as shown in SEQ ID NOS: 62 to 65;

(J) 4 types of primers each having a nucleotide sequence that is complementary to each of the nucleotide sequences as described in (I) above;

(K) 4 types of primers each having a nucleotide sequence that is identical to or substantially identical to each of the nucleotide sequences as shown in SEQ ID NOS: 67 to 70;

(L) 4 types of primers each having a nucleotide sequence that is complementary to each of the nucleotide sequences as described in (K) above;

(M) 4 types of primers each having a nucleotide sequence that is identical to or substantially identical to each of the nucleotide sequences as shown in SEQ ID NOS: 71 to 74;

(N) 4 types of primers each having a nucleotide sequence that is complementary to each of the nucleotide sequences as described in (M) above;

(O) 4 types of primers each having a nucleotide sequence that is identical to or substantially identical to each of the nucleotide sequences as shown in SEQ ID NOS: 73 to 76;

(P) 4 types of primers each having a nucleotide sequence that is complementary to each of the nucleotide sequences as described in (O) above;

(Q) 4 types of primers each having a nucleotide sequence that is identical to or substantially identical to each of the nucleotide sequences as shown in SEQ ID NOS: 73, 74, 77, and 78; and (R) 4 types of primers each having a nucleotide sequence that is complementary to each of the nucleotide sequences as described in (Q) above.

Among the methods of detecting *H. influenzae* of the present invention, the method of detecting Hib is characterized in that the above-described LAMP primer set is any one of LAMP primer sets comprising the primers as described in the following (S) to (Z):

(S) the 4 types of primers according to claim 6(A), and a primer having a nucleotide sequence that is identical to or substantially identical to the nucleotide sequence as shown in SEQ ID NO: 47 in the sequence listing;

(T) the 4 types of primers according to claim 6(B), and a primer having a nucleotide sequence that is identical to or substantially identical to a nucleotide sequence complementary to the nucleotide sequence as shown in SEQ ID NO: 47 in the sequence listing;

(U) the 4 types of primers according to claim 6(C), and a primer having a nucleotide sequence that is identical to or substantially identical to the nucleotide sequence as shown in SEQ ID NO: 52 in the sequence listing;

(V) the 4 types of primers according to claim 6(D), and a primer having a nucleotide sequence that is identical to or substantially identical to a nucleotide sequence complementary to the nucleotide sequence as shown in SEQ ID NO: 52 in the sequence listing;

(W) the 4 types of primers according to claim 6(E), and a primer having a nucleotide sequence that is identical to or substantially identical to the nucleotide sequence as shown in SEQ ID NO: 57 in the sequence listing;

(X) the 4 types of primers according to claim 6(F), and a primer having a nucleotide sequence that is identical to or substantially identical to a nucleotide sequence complementary to the nucleotide sequence as shown in SEQ ID NO: 57 in the sequence listing;

(Y) the 4 types of primers according to claim 6(I), and a primer having a nucleotide sequence that is identical to or substantially identical to the nucleotide sequence as shown in SEQ ID NO: 66 in the sequence listing; and (Z) the 4 types of primers according to claim 6(J), and a primer having a nucleotide sequence that is identical to or substantially identical to a nucleotide sequence complementary to the nucleotide sequence as shown in SEQ ID NO: 66 in the sequence listing.

The primer set for detecting *H. influenzae* of the present invention is characterized in that it is any one of the LAMP primer sets according to claims 1 to 7.

The kit for detecting *H. influenzae* of the present invention is characterized in that it comprises the LAMP primer sets according to claims 1 to 7.

BRIEF DESCRIPTION OF THE DRAWINGS

FIG. 8 is a table showing the primer sets of the examples in the first embodiment.

FIG. 9 is a table showing the results of the specificity confirmation test in the first embodiment.

FIG. 10 is a table showing the results of the sensitivity confirmation test in the first embodiment.

FIG. 11 shows the results of the clinical detection test in the first embodiment.

FIG. 12 is a view showing the position of the LAMP primer set of Example 11, which corresponds to that in the capsulation locus region II of Hib.

FIG. 14 is a table showing the primer sets of the examples in the second embodiment.

FIG. 15 is a table showing the results of the specificity confirmation test in the second embodiment, in which various capsular serotype and non-encapsulated type *H. influenzae* have been used.

FIG. 16 is a table showing the results of the specificity confirmation test in the second embodiment, in which strains other than *H. influenzae* have been used.

FIG. 18 is a table showing the results of the sensitivity confirmation test in the second embodiment.

FIG. 23(A) is a view showing the structure of each primer of the LAMP primer set of Example 1, and FIG. 23(B) is a view showing the structure of each primer of the LAMP primer set of Example 11.

BEST MODES FOR CARRYING OUT THE INVENTION

Next, the embodiments of the present invention will be described using drawings as references.

First Embodiment

The method of detecting *H. influenzae* of the present embodiment comprises amplifying nucleic acid according to the LAMP method using nucleic acid contained in an analyte as a template, and determining the presence or absence of *H. influenzae* based on the presence or absence of the amplified product, so as to detect *H. influenzae*.

The LAMP primer set used in the detection method of the present embodiment targets a P6 protein gene encoding a P6 protein that is a surface protein characteristic of *H. influenzae*.

In the above primer set, all primers have a nucleotide sequence that is identical to or complementary to a partial nucleotide sequence in a nucleotide region located downstream of bp 90 of the P6 protein gene of *H. influenzae*, and at least one primer has a nucleotide sequence that is identical to or substantially identical to a partial nucleotide sequence in the nonhomologous region ranging from bp 90 to 183, or from bp 337 to 462 of the P6 protein gene of *H. influenzae*, or a nucleotide sequence complementary thereto. Examples of such a LAMP primer set include those as described in Examples 1 to 9.

Figure 1:
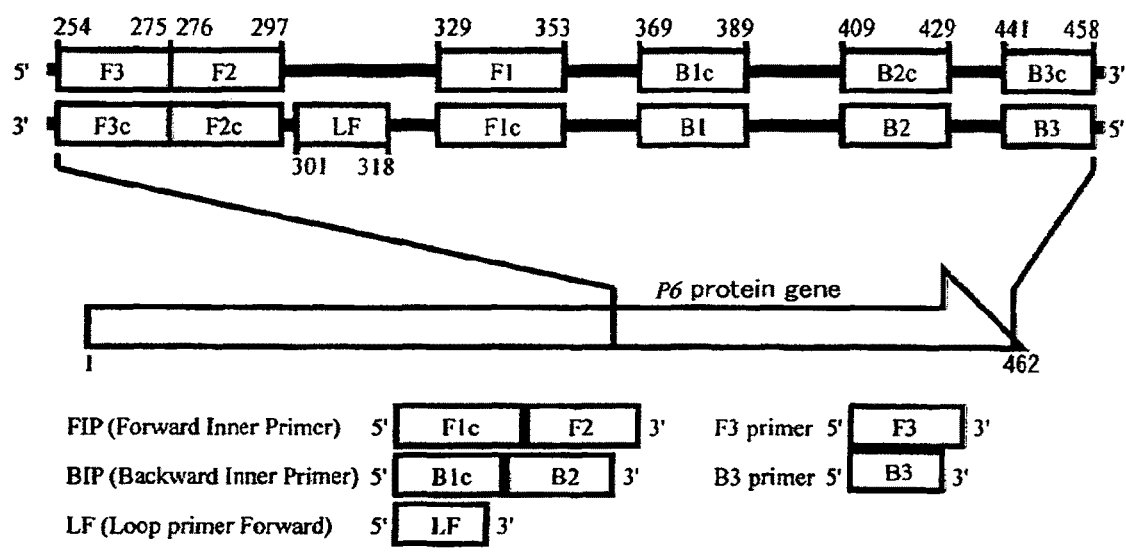
FIG. 1 is a view showing the position of the LAMP primer set of Example 1, which corresponds to that in the P6 protein gene, and the structure of each primer of the LAMP primer set of Example 1.
Figure 2:
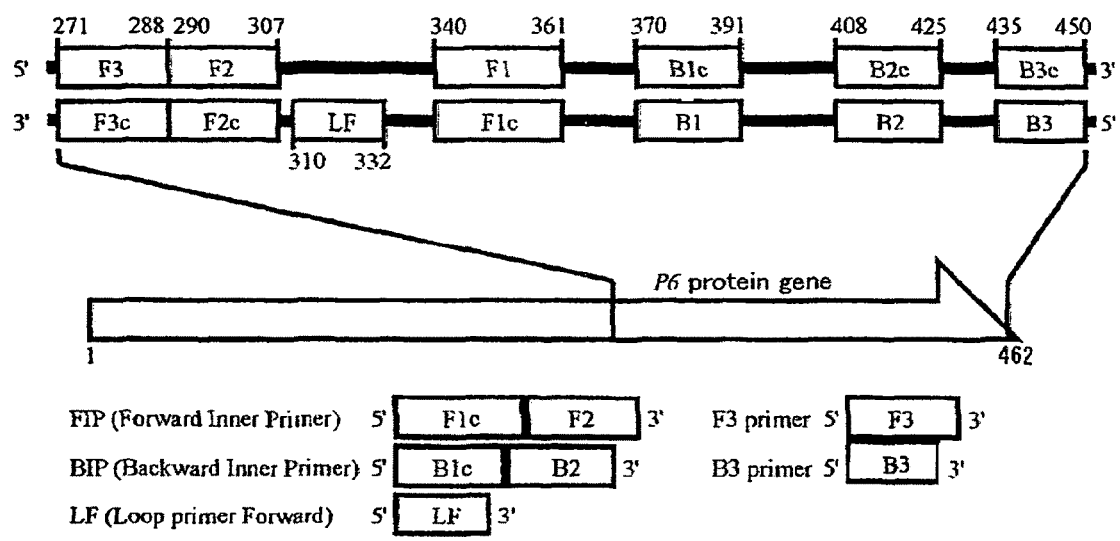
FIG. 2 is a view showing the position of the LAMP primer set of Example 2, which corresponds to that in the P6 protein gene, and the structure of each primer of the LAMP primer set of Example 2.

FIG. 1 shows the position of the LAMP primer set of Example 1, given as an example of the present embodiment, which corresponds to that in the P6 protein gene, and the structure of each primer of the above LAMP primer set. FIG. 2 shows the position of the LAMP primer set of Example 2, given as another example of the present invention, which corresponds to that in the P6 protein gene, and the structure of each primer of the above LAMP primer set. In addition, FIG. 8 shows the correlation between the primers of the examples and sequence numbers in the sequence listing representing the nucleotide sequences of the above primers.

In the P6 protein gene region, a nucleotide sequence identical to or substantially identical to a partial nucleotide sequence in the nonhomologous region ranging from bp 90 to 183, or from bp 337 to 462, or a nucleotide sequence complementary to thereto, becomes a nonhomologous region, which consists of contiguous nucleotides that are different between *H. influenzae* and *H. parainfluenzae*. In the present embodiment, as many partial nucleotide sequences as possible in this region are incorporated into a primer, so as to impart excellent specificity to the primer.

The LAMP primer set is constituted by the combination of 6 different regions on a target gene (P6 protein gene) (F3, F2, F1, B1c, B2c and B3c from the 5' end side), regions complementary to the above regions (B3, B2, B1, F1c, F2c and F3c from the 5' end side), and an LF region existing between F1c and F2c. The LAMP primer set of Examples 1 and 2 comprises a Forward Inner Primer (hereinafter abbreviated as "FIP" at times) produced by ligating the F1c region and the F2 region from the 5' end side, a Backward Inner Primer (hereinafter abbreviated as "BIP" at times) produced by ligating the B1c region and the B2 region from the 5' end side, a F3 primer consisting of the F3 region, a B3 primer consisting of the B3 region, and a Loop primer Forward consisting of the LF region (hereinafter abbreviated as "LF" at times). This LF is not a primer that is essential for the reaction, but a primer that is arbitrarily designed for the improvement of the reaction rate. Thus, it is also possible to use a primer set that does not comprise this LF (for example, only 4 types of primers having the nucleotide sequences as shown in SEQ ID NOS: 1 to 4). There are also cases where LF may not be designed, but a Loop primer Back (hereinafter abbreviated as "LB" at times), which is not shown in the figures, may be designed between the B2 region and the B1 region, depending on the position at which the primer set is designed.

An amplification mechanism with such a LAMP primer set is described, in detail, in Publicly Known Document 1 ("Nucleic Acid Research", 2000, Vol. 28, No. 12, e63) and Publicly Known Document 2 (K. Nagmine & two other people, "Accelerated reaction by loop-mediated isothermal amplification using loop primers", Molecular and Cellular Probes, 2002, Vol. 16, pp. 223-229). If 6 regions comprised in 4 types of primers do not function as designed, the synthetic reaction of the present invention does not progress. Thus, the occurrence of a non-specific amplification reaction that is associated with the synthesis of a non-specific complementary strand by accident is effectively prevented, and the specificity of the amplification reaction is thereby high.

The aforementioned primer used in detection of *H. influenzae* can be chemically synthesized using a DNA automatic synthesizer, for example. Otherwise, the above primer can be prepared by modification, such as a step of cleaving natural nucleic acid with restriction enzymes and a step of allowing the obtained cleavage product to bind to another cleavage product.

It is to be noted that the term "primer" is used in the present invention to mean an oligonucleotide, which has a certain nucleotide sequence as described above, which is able to form a base pair with other nucleotides, and which comprises a —OH group acting as a base point for complementary strand synthesis at the 3' end thereof. Accordingly, as long as these conditions are satisfied, the backbone thereof is not necessarily limited to the backbone formed based on a phosphodiester bond. For example, a primer having a backbone that is not P but S, consisting of peptide nucleic acid formed based on a phosphothioate form or a peptide bond, may also be used. In addition, a primer labeled with a known labeling substance may also be used. Examples of such a labeling substance include a binding ligand such as digoxin or biotin, an enzyme, a fluorescent substance, a scintillating material, and a radioactive element. Moreover, it is also possible to allow the primer of the present invention itself to bind to a solid phase, as in the case of a DNA chip and the like. When such a solid-phased primer is used as a synthesis initiation point, the synthetic reaction product of nucleic acid is captured by the solid phase, so that separation and detection can be easily carried out.

After preparation of a LAMP primer set, DNA polymerase used in the strand displacement-type synthesis of a complementary strand and a nucleotide acting as a substrate of the DNA polymerase are added to the LAMP primer set, so as to carry out a LAMP reaction.

The type of the DNA polymerase that can be used in the present invention is not particularly limited, as long as it has strand displacement activity. Examples of such an enzyme include Bst DNA polymerase (large fragment), Bca (exo-) DNA polymerase, Klenow fragment of *Escherichia coli* DNA polymerase 1, Vent (exo-) DNA polymerase (obtained by removing exonuclease activity from Vent DNA polymerase), DeepVent (Exo-) DNA polymerase (obtained by removing exonuclease activity from DeepVent DNA polymerase), and KOD DNA polymerase. A preferred example is Bst DNA polymerase (large fragment). When such Bst DNA polymerase is used, it is preferable to carry out the reaction at a temperature between approximately 60° C. and 65° C., which is the optimal reaction temperature.

Furthermore, known techniques can be applied to detect an amplified product. For example, the aforementioned labeled oligonucleotide is used to detect a labeling substance, or the reaction solution obtained after completion of the reaction is directly subjected to agarose electrophoresis, so as to easily detect an amplified product.

Still further, since gene amplification is efficiently carried out with accelerating speed according to the LAMP method, ethidium bromide, SYBR (registered trade mark) Green I, or the like, which is an intercalator specifically incorporated into a molecule of double-stranded nucleic acid, have previously been added to the reaction solution, so as to confirm amplification. Further, in the LAMP method, a large amount of substrate is consumed as a result of the synthesis of nucleic acid, and pyrophosphoric acid as a by-product reacts with magnesium that co-exists therewith, so that it becomes magnesium pyrophosphate. As a result, the reaction solution becomes clouded to such an extent that it can be confirmed by naked eyes. Such white turbidity is observed after completion of the reaction, or an increase in the turbidity during the reaction is measured using a measurement apparatus capable of optically observing such an increase in the turbidity over time. For example, a change in the absorbance at 650 nm is measured using a common spectrophotometer, so as to confirm amplification.

Various types of reagents necessary for such a LAMP reaction have previously been packaged, so that the reagents can be supplied as a kit for detecting *H. influenzae*. Specifically, the above kit comprises the aforementioned LAMP primer set used in detection of *H. influenzae*, dNTP used as a substrate for complementary strand synthesis, DNA polymerase used in the strand displacement-type synthesis of a complementary strand, a buffer solution giving preferred conditions to an enzyme reaction, and as necessary, reagents necessary for detection of the synthetic reaction product.

Thus, in the LAMP method, it is possible to promote an amplification reaction only by performing isothermal incubation at a temperature in which enzyme activity can be maintained. Accordingly, differing from the PCR method, the LAMP method does not need equipment for regulation of temperature, and this method enables easy detection at low cost. At the same time, this method does not have any waste of time caused by temperature change, and thus it enables rapid detection.

Examples in the First Embodiment

The first embodiment will be specifically described in the following examples. However, these examples are not intended to limit the scope of the present invention.

(Concerning Specificity Confirmation Test)

The method of detecting *H. influenzae* of the present embodiment was carried out, and the specificity of the detection method of the present embodiment was confirmed. The specificity confirmation test will be described below.

(1) Preparation of Chromosomal DNA

First, chromosomal DNA was purified from various types of strains to be used in the test, and DNA used as a template for an amplification reaction was prepared.

Chromosomal DNA was obtained by extracting such DNA from various types of strains using Dr. GenTLE (registered trade mark; manufactured by TAKARA BIO INC.) used for enzymes, and then purifying it using QIAamp (registered trade mark) DNA mini kit (manufactured by QIAGEN). Extraction and purification were carried out in accordance with the manuals included with the above kits.

In this test, chromosomal DNA was extracted from a total of 28 types of strains, which are classified into 9 types of *H. influenzae* and 19 types of strains other than *H. influenzae* (including one type of *H. parainfluenzae*), and was then used. These 28 strains are shown in FIG. 9.

(2) Concerning Lamp Reaction and PCR Reaction

Next, using the LAMP primer sets of Examples 1 to 9 and Comparative examples 2 and 3 of the present embodiment (refer to FIG. 8), a LAMP reaction was carried out with the chromosomal DNA derived from various types of strains prepared in (1) above as a template.

A LAMP reaction solution (25 µl) was prepared by mixing 40 pmol each of FIP and BIP, 5 pmol each of the F3 primer and the B3 primer, 10 pmol of the LF primer, 8 U of Bst DNA polymerase large fragment (manufactured by New England Biolabs), deoxynucleoside triphosphate (1.4 mM each), betaine (0.8 M), Tris-HCl buffer (20 mM; pH 8.8), KCl (10 mM), $(NH_4)_2SO_4$ (10 mM), $MgSO_4$ (8 mM), 0.1% Tween 20, and 2 µl of the template DNA solution prepared as described in (1) above.

Thereafter, the LAMP reaction solution was incubated at 63° C. for 60 minutes, so as to promote the LAMP reaction. Finally, the reaction solution was heated at 80° C. for 2 minutes, so as to terminate the reaction.

In addition, the PCR reaction was also carried out, so as to compare with detection by the LAMP method (Comparative example 1).

At the time, a publicly known PCR primer set, which targets a P6 protein gene encoding a P6 protein, was used (described in Reference 1 in the "Background Art" section). The sequences are shown in SEQ ID NOS: 13 and 14 (Comparative example 1). It is to be noted that the targeted position of this primer set (region to be amplified) is a region ranging from bp 122 to 434.

A PCR reaction solution (10 µl) was prepared by mixing deoxynucleoside triphosphate (0.2 mM each), Tris-HCl buffer (10 mM; pH 8.3), KCl (50 mM), $MgCl_2$ (2 mM), 1 U ExTaq DNA polymerase (manufactured by TAKARA BIO INC.), a forward primer and a reverse primer (each 0.5 µM), and 1 µl of a template DNA solution.

The PCR reaction was carried out for 30 cycles using Thermal Cycler (manufactured by MJ Research). In each cycle, denaturation at 95° C. for 30 seconds, annealing at 55° C. for 1 minute, and synthesis at 72° C. for 2 minutes were successively carried out. Finally, heating at 72° C. for 2 minutes was carried out, so as to terminate the reaction.

(3) Concerning Confirmation of Presence or Absence of Amplification

The presence or absence of amplification as a result of the LAMP reaction was detected by directly looking at the reaction tube by eyes, and observing the presence or absence of white turbidity of the LAMP reaction solution. That is to say, when a replication sequence exists, magnesium pyrophosphate is generated as a by-product of the reaction in an amount that is proportional to the amount of the replication sequence, and the LAMP reaction solution thereby becomes clouded. On the other hand, when such a replication sequence does not exist, the LAMP reaction solution remains transparent.

Moreover, the presence or absence of amplification as a result of the LAMP reaction was also confirmed by agarose gel electrophoresis performed on the amplified product. At the time, each of the amplified product itself and a product obtained by digestion of the amplified product with the restriction enzyme TasI (manufactured by Fermentas) was electrophoresed in 3% agarose gel. Thereafter, the resultant was stained with ethidium bromide, so as to confirm the electrophoretic pattern. When the amplified product was directly electrophoresed, the replication sequence appeared as a ladder pattern that is characteristic of the LAMP reaction. When the product digested with the restriction enzyme was electrophoresed, the replication sequence appeared in the form of fragments having a size of 90 bp or 125 bp in the case of Example 1, and fragments having a size of 88 bp or 99 bp in the case of Example 2. Thereafter, BigDye Terminator V3.1 cycle sequencing kit (manufactured by Applied Biosystems) was used to carry out a sequencing reaction, and ABI PRISM 377 DNA sequencer (manufactured by Applied Biosystems) was then used to carry out sequencing analysis, so as to confirm whether or not the target portion had been amplified. In this sequencing reaction, the sequences of F2 and B2 as shown in FIG. 1 were used as primers in Example 1, and the sequences of F2 and B2 as shown in FIG. 2 were used as primers in Example 2.

On the other hand, the presence or absence of the amplified product obtained as a result of the PCR of Comparative example 1 was also confirmed by subjecting the amplified product (2 μl) to 3% agarose gel electrophoresis.

(4) Concerning Test Results

The results of the aforementioned test are shown in FIG. 9. With regard to the results, "+" indicates a case where amplification (white turbidity) was confirmed by visual observation after completion of the incubation for 60 minutes, and "−" indicates a case where such amplification was not confirmed by visual observation after completion of the incubation for 60 minutes. In FIG. 9, the superscript notation "a" indicates that the strain had been obtained from Department of Microbiology, Nihon University School of Dentistry. The superscript notation "b" indicates that the strain had been obtained from Department of Microbiology, Gifu University School of Medicine. The superscript notation c indicates that the strain had been obtained from the Institute of Medical Science, the University of Tokyo.

Figure 3:
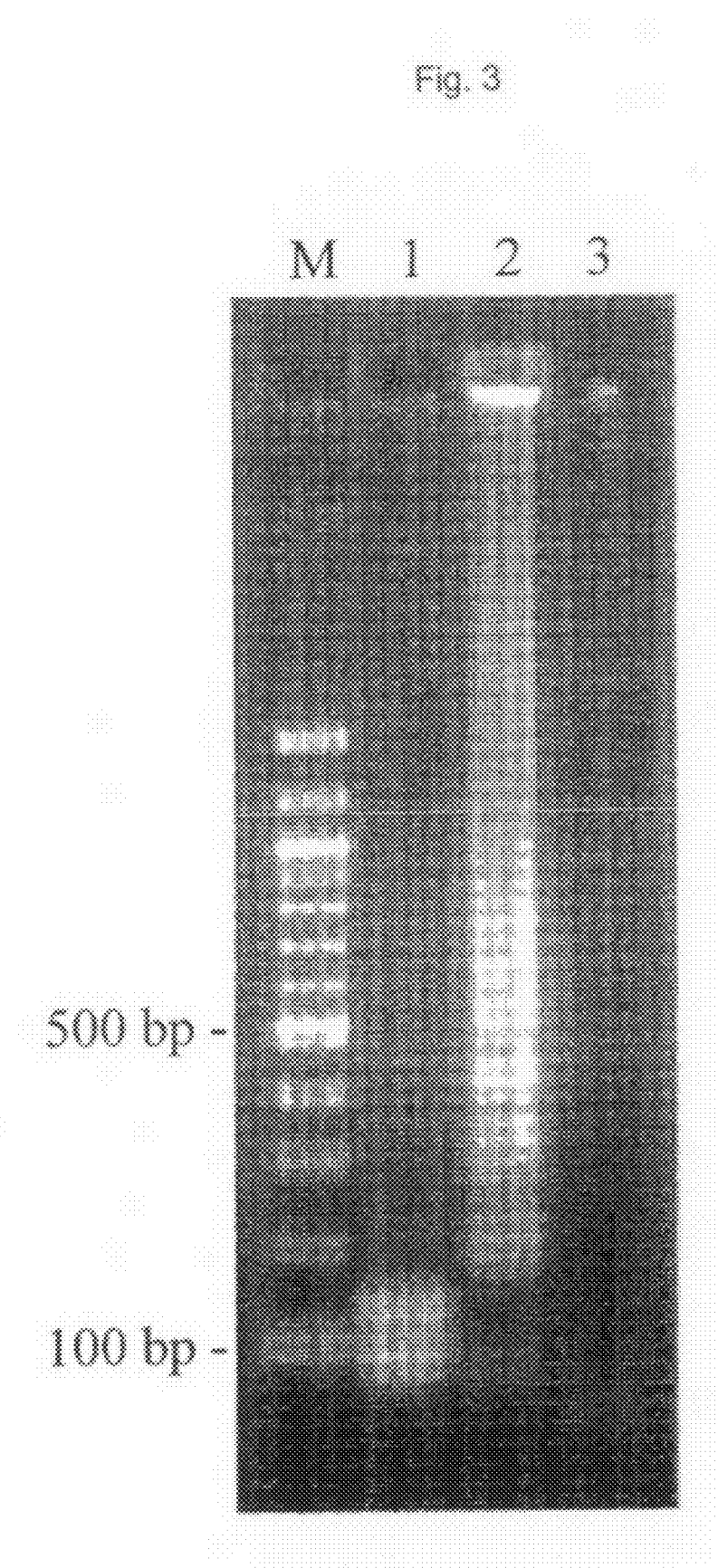
FIG. 3 is a photograph of the gel obtained by electrophoresing an amplified product obtained after a LAMP reaction (Example 1).
Figure 4:
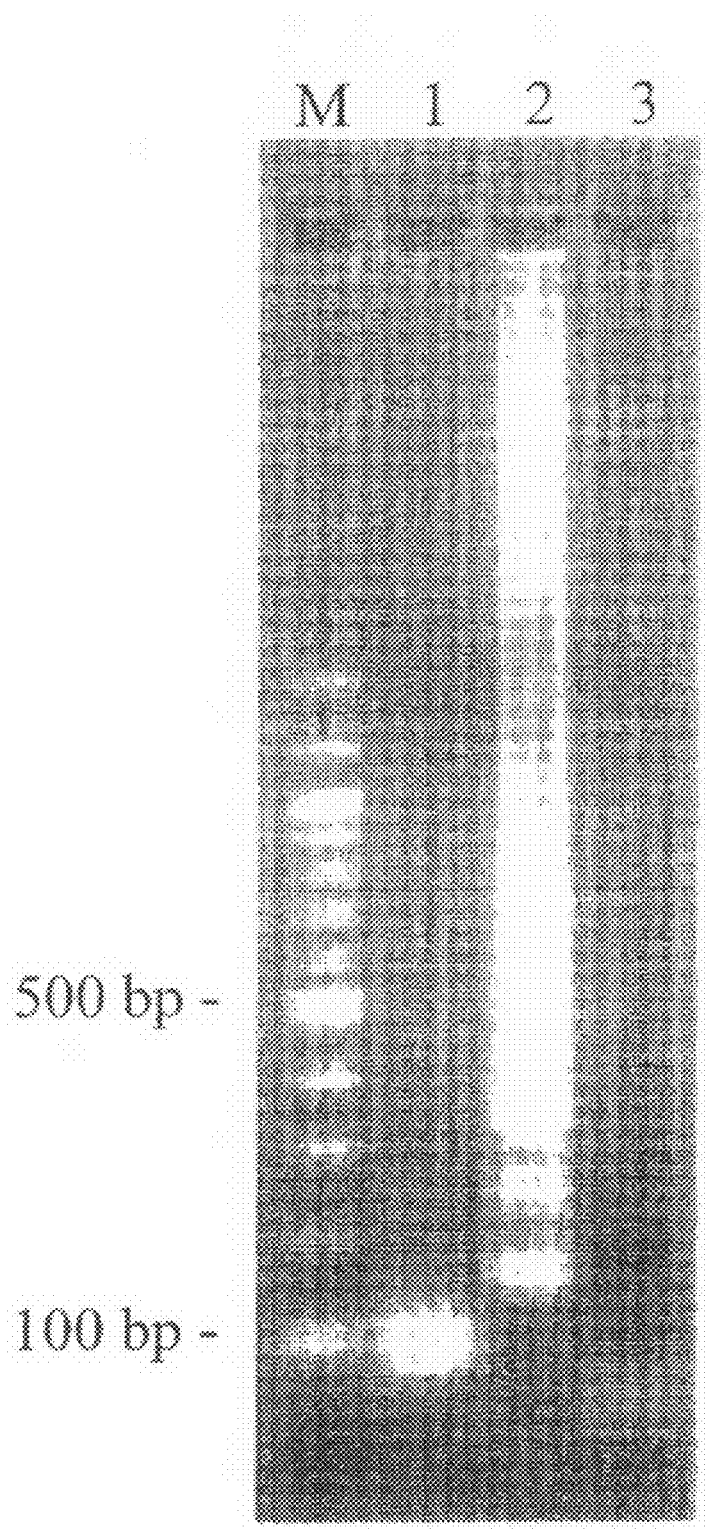
FIG. 4 is a photograph of the gel obtained by electrophoresing an amplified product obtained after a LAMP reaction (Example 2).
Figure 5:
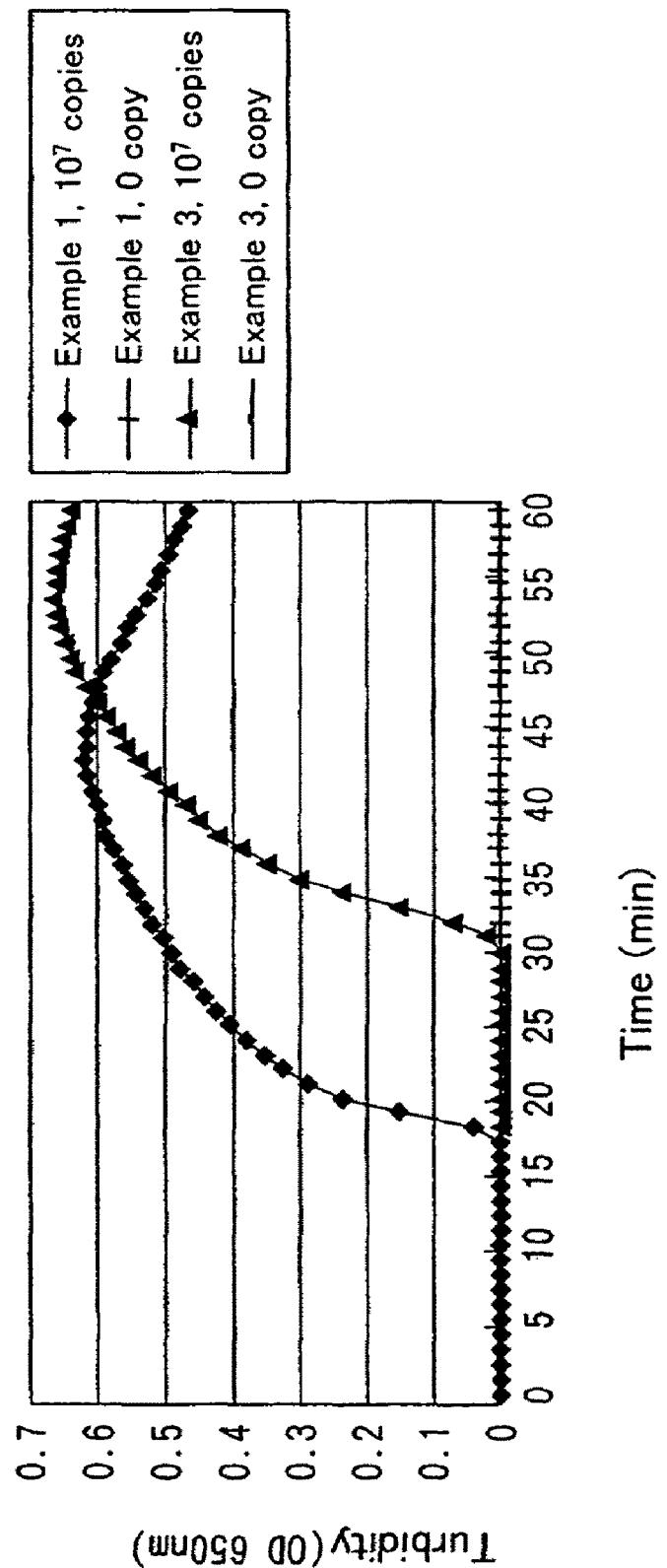
FIG. 5 is a graph showing a change in turbidity in the LAMP reactions of Examples 1 and 3.

As a result, as shown in FIG. 9, when *H. influenzae* was used as a template, even if any one of the LAMP primer sets of Examples 1 to 9 was used, a large amount of amplified product was confirmed after completion of the incubation for 60 minutes. In contrast, in the case of all other strains including *H. parainfluenzae*, after completion of the incubation for 60 minutes, no amplified products were confirmed. Such results corresponded to the results of electrophoresis. Each of FIGS. 3 and 4 shows a photograph of the gel obtained by performing electrophoresis on the amplified product obtained after the LAMP reaction. Lane M on both sides is a lane obtained by feeding a marker for indicating intervals of 100 bp. Lane 1 is a lane obtained by treating the amplified product of lane 2 with TasI and then electrophoresing the resultant. Lane 2 is a lane obtained by electrophoresing an amplified product obtained when the template DNA concentration was set at $10^6$ copies. Lane 3 is a lane obtained by electrophoresing an amplified product obtained when the template DNA concentration was set at 0 copy. In the case of lane 2, the amplified product had a ladder electrophoretic pattern. It was thereby confirmed that the amplified product had an inversed portion, and that it adopted a stem-loop structure characteristic of the LAMP reaction. In addition, in lane 1 of FIG. 3, the sections of 90 bp and 125 bp of Example 1 had appeared (sections of 88 bp and 99 bp of Example 2 in the case of FIG. 4), and thus it was confirmed that a portion to be targeted had been amplified. Moreover, the amplified product was also subjected to sequencing analysis. As a result, the sequence amplified as a result of the LAMP reaction matched with an anticipated sequence.

On the other hand, in the case of detection according to the PCR method, both *H. influenzae* and *H. parainfluenzae* were detected, and thus the two types of strains could not be distinguished from each other. Furthermore, in Comparative example 2 in which the LAMP primer set that was outside of the scope of the present invention was used, neither *H. influenzae* nor other strains were detected.

From these results, it was confirmed that the method of detecting *H. influenzae* of the present invention is excellent in terms of specificity, and that the above method is able to distinguish *H. influenzae* from *H. parainfluenzae*.

(Concerning Sensitivity Confirmation Test)

Next, detection sensitivity was confirmed using each of the primer sets of the aforementioned Examples and Comparative examples 1 to 3. Such detection sensitivity will be described below.

(1) Preparation of Chromosomal DNA

In the present test, as in the case of the specificity confirmation test, chromosomal DNA was purified from *H. influenzae* IID984, and it was then used as a template. The template DNA concentration (copy number) in the reaction solution was assayed, at a molecular size of 1.9 Mbp, using Ultrospec 3300 Pro spectrophotometer (manufactured by Amersham Pharmacia Biotech).

(2) LAMP Method and PCR Method

The template DNA solution, which had previously been assayed as described in (1) above, was diluted with a stepwise of 10 times, so as to prepare a solution that was diluted by a factor between 1 and 1,000,000. Using this solution as a template DNA solution for the LAMP reaction, a detection limit was confirmed. It is to be noted that the LAMP reaction solution was the same as that used in the aforementioned specificity confirmation test in terms of the additive amount of the template DNA solution and the additive amounts of other additives, with the exception that the concentration of the template DNA solution was different. In addition, with regard to the LAMP reaction, the reaction solution was incubated at 63° C. for 35 minutes or 60 minutes, so as to promote the reaction. Finally, the reaction solution was heated at 80° C. for 2 minutes, so as to terminate the reaction.

Moreover, in order to compare with the detection method of the present invention, amplification and detection were carried out also by the PCR method (Comparative example 1). At the time, the same template DNA solution as that used in the LAMP reaction was used as a template DNA solution for the PCR reaction, so as to confirm a detection limit. The PCR reaction solution was the same as that used in the aforementioned specificity confirmation test in terms of the additive amount of the template DNA solution and the additive amounts of other additives, with the exception that the concentration of the template DNA solution was different. Conditions for the PCR reaction were also the same as those applied to the aforementioned specificity confirmation test.

(3) Concerning Confirmation of Presence or Absence of Amplification

With regard to the presence or absence of amplification as a result of the LAMP reaction, turbidity was measured using Loopamp (registered trade mark) real-time turbidity measurement apparatus (manufactured by TERAMECS Co., Ltd.; Model: LA-200). When the turbidity was 0.1 or greater, it was determined that amplification had been carried out.

Moreover, as with the aforementioned specificity confirmation test, the presence or absence of white turbidity was confirmed by visual observation, and it was also confirmed by electrophoresis.

Furthermore, the presence or absence of an amplified product generated as a result of PCR in Comparative example 1 was also confirmed by subjecting the amplified product (2 μl) to 3% agarose gel electrophoresis.

(4) Concerning Test Results

With regard to the test results, "+" indicates a case where an amplified product was confirmed as described above, and "−" indicates a case where such amplification was not confirmed. The test results are shown in FIG. 10.

As shown in FIG. 10, in the detection method using the LAMP primers of Examples 1 and 2, an amplified product could be detected by carrying out the LAMP reaction for 60 minutes, even in a case where the concentration of template DNA was 100 copies. The detection sensitivity of the above detection method was 10 times greater than those of other Examples and Comparative example 1 in which PCR primers were used, and thus it was confirmed that the above detection method is excellent in terms of sensitivity. On the other hand, in the case of Comparative examples 2 and 3, *H. influenzae* was not detected, even in a case where the template DNA concentration was $10^6$ copies. Moreover, as shown in FIG. 10, in Examples 1 and 2, when the template DNA concentration was $10^3$ copies, it was possible to detect *H. influenzae* for 35 minutes. Thus, it was confirmed that the above detection method is excellent in terms of sensitivity and promptness.

(Concerning Clinical Detection)

With regard to Example 1 and Comparative example 1, clinical detection was carried out. Such clinical detection will be described below.

First, 9 types of strains were separated from an oral sample. Thereafter, each of the separated 9 types of strains was cultured in horse blood medium, and the hemolytic pattern thereof was confirmed. Thus, the V factor (NAD) and X factor (hemin) requirement was confirmed, and at the same time, API 20 NH (manufactured by bioMerieux) was performed to identify the bacterial species. As a result, as shown in FIG. 11, 3 types of *H. influenzae*, 4 types of *H. parainfluenzae*, and 2 types of *H. parahaemolyticus* were identified. In addition, PCR was carried out according to the method described in Publicly Known Document 3, and a Bex A protein gene associated with capsule formation was targeted, so as to confirm that the 3 types of *H. influenzae* were of the non-encapsulated type (Publicly Known Document 3: van Ketel, R. J., B. de Wever, and L. van Alphen. 1990. Detection of *Haemophilus influenzae* in cerebrospinal fluids by polymerase chain reaction DNA amplification. J. Med. Microbiol. 33: 271-276).

As stated above, the chromosomal DNA of each strain as isolated and identified above was used as a template, and $10^6$ copies as a template DNA concentration were subjected to the LAMP reaction and the PCR reaction, using the primer sets of Example 1 and Comparative example 1. The LAMP reaction was carried out for 60 minutes. A case where white turbidity could be confirmed by visual observation was defined as "+," and a case where such white turbidity could not be confirmed was defined as "−." On the other hand, regarding the PCR reaction, detection was confirmed by agarose gel electrophoresis.

As a result, as shown in FIG. 11, only *H. influenzae* was detected in Example 1, but a positive reaction was exhibited not only regarding *H. parainfluenzae* but also regarding *H. parahaemolyticus*. From these results, it was confirmed that even in clinical detection, Example 1 was excellent in terms of specificity and detection reliability.

(Concerning Real-Time Turbidity Measurement Test)

(1) Concerning Detection Promptness

A test to confirm the detection promptness of the primer sets of Examples 1 to 9 and Comparative examples 2 and 3 was carried out. In the present test, the template DNA concentration was set at $10^6$ copies, and each primer set was added thereto. Thereafter, the composition of the LAMP reaction solution and conditions for the LAMP reaction were determined to be the same as those as described above, and the LAMP reaction was then carried out. During the reaction, using Loopamp (registered trade mark) real-time turbidity measurement apparatus (manufactured by TERAMECS Co., Ltd.), the absorbance at 650 nm was read out every 6 seconds, and the threshold time (Tt: the time required until the turbidity exceeds 0.1) was then measured.

The results are shown in FIG. 8. As shown in FIG. 8, the threshold times of Examples 1 and 2 were significantly short when compared with other examples, and thus it was confirmed that *H. influenzae* could be detected significantly rapidly in Examples 1 and 2. On the other hand, in the case of Comparative example 2, in which specificity had not been confirmed in the aforementioned specificity confirmation test, the threshold time was significantly slow (109 minutes) when compared with examples even in the present test. Thus, it is assumed that the reaction is unstable in Comparative example 2. In the case of Comparative example 3 having the same target position (a region between the F3 primer and the B3 primer), the set position of each primer was changed, so that the threshold time was somewhat improved. However, there was still a large difference from other examples. Thus, it was difficult to obtain a LAMP primer enabling a stable and rapid reaction within the above range.

(2) Concerning Quantitative Capability

Next, the following test was carried out on Example 1 that is excellent in terms of specificity, sensitivity, and promptness. First, the template DNA copy number was adjusted to be 0 to $10^6$ per reaction tube, and the LAMP primer set of Example 1 was added thereto. Thereafter, the composition of the LAMP reaction solution and conditions for the LAMP reaction were determined to be the same as those as described above, and the LAMP reaction was then carried out. During the reaction, using the aforementioned real-time turbidity measurement apparatus, the absorbance at 650 nm was read out every 6 seconds.

Figure 6:
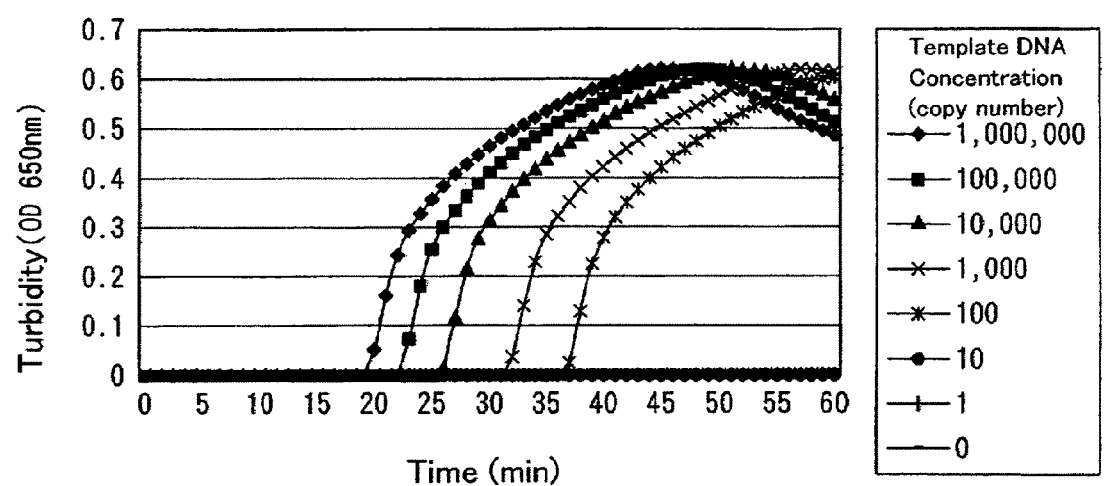
FIG. 6 is a graph showing the results of the real-time turbidity measurement of Example 1.

As a result, as shown in FIG. 6, it was confirmed that when the copy number of template DNA is 100 copies or greater, the turbidity becomes 0.1 or greater within 60 minutes. Such results correspond to the results regarding the presence or absence of amplification obtained by visual observation and electrophoresis in the aforementioned sensitivity test. Moreover, it was also confirmed that as the initial amount of template DNA increases, the threshold time becomes shorter.

Figure 7:
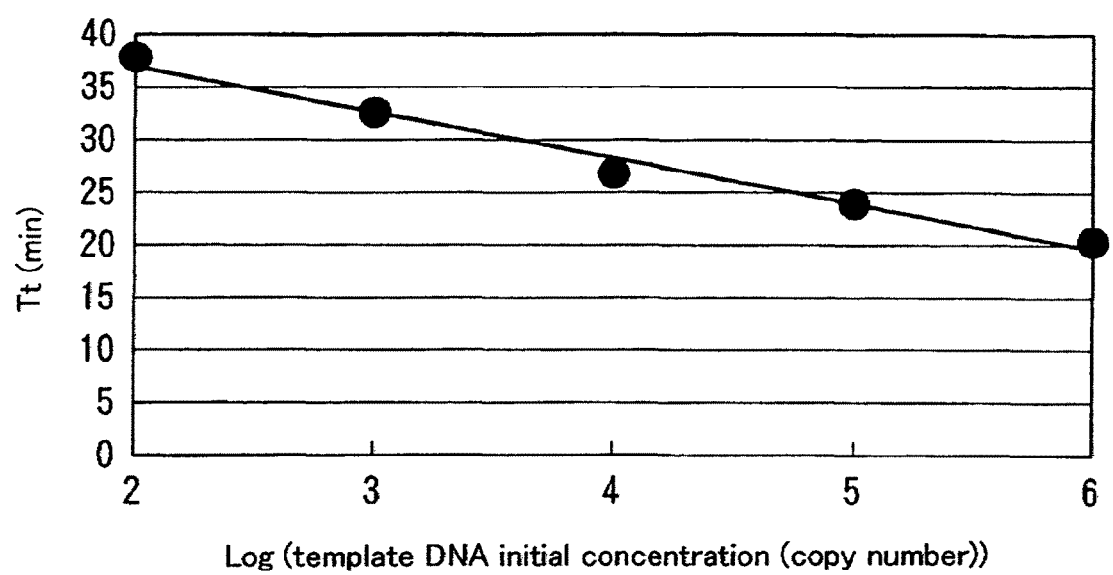
FIG. 7 is a graph showing the relationship between the turbidity as shown in FIG. 6 and the common logarithm of the amount of template DNA.

FIG. 7 shows the relationship between the threshold time in the case of Example 1 and the common logarithm of the initial amount of template DNA. Linearity was observed between such two factors, and a high correlation (correlation coefficient $r^2$=0.978) was obtained. As Mori et al. have reported in 2004, this means that when the initial concentration of DNA derived from *H. influenzae* is unknown, not only the presence or absence of the DNA, but also the concentration thereof can be assayed (Mori, Y. & three other people, "Real-time turbidimetry of LAMP reaction for quantifying template DNA," J. Biochem. Biophys. Methods, Vol. 59, pp. 145-157). That is to say, for example, even regarding a sample whose concentration is unknown, diluted solutions having different dilution ratios are prepared, and the LAMP reaction is carried out using each diluted solution. Thereafter, the threshold time is measured, so as to produce a regression line. Thus, from the regression line, the initial concentration of template DNA, which has been unknown, can be determined.

As stated above, according to the detection method of the present embodiment, *H. influenzae* can be distinguished from *H. parainfluenzae*, which have not been distinguished from each other according to the conventional PCR method. Thus, it was confirmed that the above detection method is excellent in terms of specificity. In particular, differing from the conventional PCR primers, the LAMP primers (Examples 1 and 2, for example), which target a downstream region, have high detection sensitivity, and also enable rapid detection. In addition, it is also possible to assay *H. influenzae* using such LAMP primers. Moreover, since the LAMP reaction progresses under isothermal conditions and the results can be confirmed by visual observation, it requires only simple equipment, and thereby the above detection method can be simply and rapidly carried out even in the examination room in hospital, etc.

Second Embodiment

The LAMP primer set used in the detection method of the present embodiment targets capsulation locus region II encoding the capsule of Hib. In the above primer set, all primers have a nucleotide sequence that is identical to or substantially identical to a partial nucleotide sequence in the region ranging from bp 1 to 6,653, or a nucleotide sequence complementary thereto. Examples of such a LAMP primer set include those as described in Examples 11 to 19.

Figure 13:
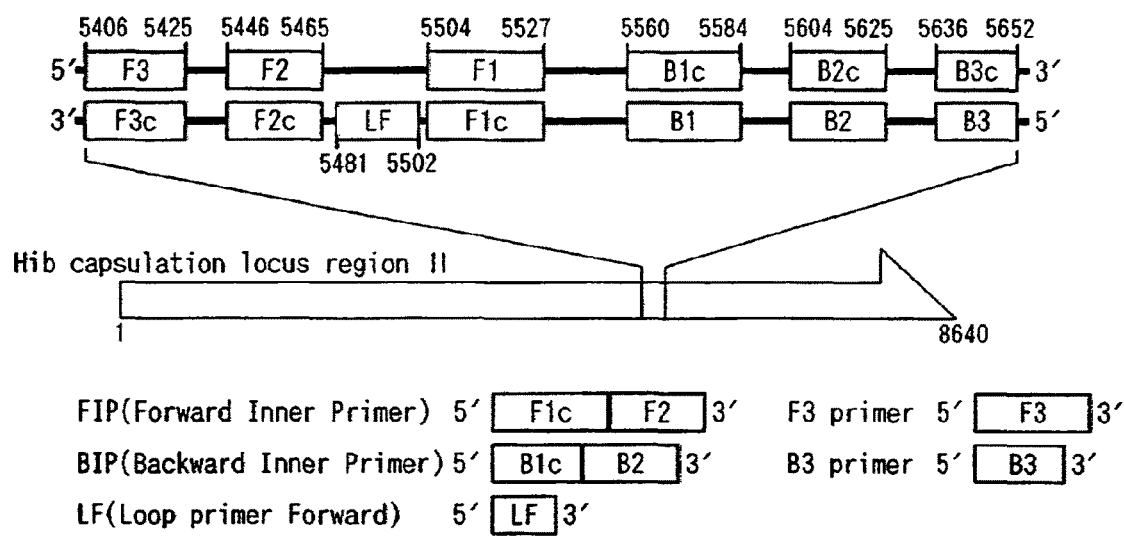
FIG. 13 is a view showing the structure of each primer of the LAMP primer set of Example 11.

FIGS. 12 and 13 show the position of the LAMP primer set of Example 11, given as an example of the present embodiment, which corresponds to that in the capsulation locus, and the structure of each primer of the above LAMP primer set. In addition, FIG. 14 shows the correlation between the primers of the examples and sequence numbers in the sequence listing representing the nucleotide sequences of the above primers.

FIG. 12 includes 7 columns. Each column consists of 2 or 3 lines. The line with the term "No." in each column indicates the positions of nucleotides, and the line with the term "Base" indicates the nucleotides in the capsulation locus region II of Hib (GenBank Accession No. X78559) in the above-described position. The line with the term "Primer" indicates the positions of primers. FIG. 12 shows a portion of the capsulation locus region II, and the entire nucleotide sequence of the capsulation locus region II is shown in SEQ ID NO: 79. In addition, the arrow in each of the "Primer" lines of FIG. 12 indicates the 5'→3' direction of the primer. Accordingly, the region, the range of which is determined by the left arrow, indicates that a region complementary to the above region acts as a primer.

The basic structure, action, and the like of the LAMP primer set are described in the first embodiment, and thus the explanation thereof is omitted herein.

Examples in the Second Embodiment

The second embodiment will be specifically described in the following examples. However, these examples are not intended to limit the scope of the present invention.

(Concerning Specificity Confirmation Test)

(1) Preparation of Chromosomal DNA

First, chromosomal DNA was purified from various types of strains to be used in the test, and DNA used as a template for an amplification reaction was prepared.

Chromosomal DNA was obtained by extracting such DNA from various types of strains and then purifying it, using QIAamp (registered trade mark) DNA mini kit (manufactured by QIAGEN). Extraction and purification were carried out in accordance with the manuals included with the above kits.

In this test, chromosomal DNA was extracted from a total of 54 types of strains, namely, 33 types of *H. influenzae* and 21 types of strains other than *H. influenzae*, and it was then used. These 54 types of strains are shown in FIGS. 15 and 16. In FIG. 15, *H. influenzae*, strain names of which are CI-1 to CI-26, had been isolated from a sample collected from nasopharynx. These strains were obtained from Department of Microbiology, Gifu University School of Medicine.

(2) Concerning LAMP Reaction

Next, using the LAMP primer sets of Examples 11 to 19 of the present embodiment (refer to FIG. 14), a LAMP reaction was carried out with the chromosomal DNA derived from various types of strains prepared in (1) above as a template.

A LAMP reaction solution (25 µl) was prepared by mixing FIP and BIP (1.6 µM each), the F3 primer and the B3 primer (0.2 µM each), the LF primer (0.4 µM), 8 U of Bst DNA polymerase large fragment (manufactured by New England Biolabs), deoxynucleoside triphosphate (1.4 mM each), betaine (0.8 M), Tris-HCl buffer (20 mM; pH 8.8), KCl (10 mM), $(NH_4)_2SO_4$ (10 mM), $MgSO_4$ (8 mM), 0.1% Tween 20, and 2 µl of the template DNA solution prepared as described in (1) above (template DNA concentration: $10^6$ copies).

Thereafter, the LAMP reaction solution was incubated at 63° C. for 60 minutes, so as to promote the LAMP reaction. Finally, the reaction solution was heated at 80° C. for 2 minutes, so as to terminate the reaction.

(3) Concerning Confirmation of Presence or Absence of Amplification

The presence or absence of amplification as a result of the LAMP reaction was detected by directly looking at the reaction tube by eyes, and observing the presence or absence of white turbidity of the LAMP reaction solution.

The presence or absence of amplification as a result of the LAMP reaction was also confirmed by performing agarose gel electrophoresis on the amplified product. The amplified product was digested with the restriction enzyme Hpy188I (manufactured by New England BioLabs), and the digest was then electrophoresed in 3% agarose gel. Thereafter, the resultant was stained with ethidium bromide to confirm the electrophoretic pattern. When the amplified product was directly subjected to the electrophoresis, a replication sequence appeared as a ladder pattern that is characteristic of the LAMP reaction. The fragments of the products obtained by digestion with the restriction enzyme, which had an estimated size (125 bp, 135 bp), were confirmed by electrophoresis. Moreover, BigDye Terminator V3.1 cycle sequencing kit (manufactured by Applied Biosystems) was used to carry out a sequencing reaction, and ABI PRISM 377 DNA sequencer (manufactured by Applied Biosystems) was then used to carry out sequencing analysis, so as to confirm whether or not the target portion had been amplified. In this sequencing reaction, the sequences of F2 and B2 as shown in FIGS. 12 and 13 were used as primers.

(4) Concerning Determination Using Serum

In order to compare with the examples of the present embodiment, the presence or absence of an aggregate generated as a result of the antigen-antibody reaction between serum containing an antibody reacting with capsule type b and the capsule type b is determined by the slide agglutination method using immune serum for capsular typing of *H. influenzae* (manufactured by Denka Seiken Co., Ltd.), so as to detect Hib.

Furthermore, Hib was detected also by the PCR method in accordance with Non-Patent Document 1. Using the obtained result as a reference, the detection results obtained using the aforementioned LAMP primer sets and the detection results obtained using serotype, were evaluated.

(5) Concerning Test Results

The results of the aforementioned test are shown in FIGS. 15 and 16. With regard to the results, "+" indicates a case where amplification (white turbidity) was confirmed by visual observation after completion of the incubation for 60 minutes, and "−" indicates a case where such amplification was not confirmed by visual observation after completion of the incubation for 60 minutes. In FIG. 15, the superscript notation "a" indicates the determination results obtained by the method described in Non-Patent Document 1. The superscript notation "b" indicates the test results obtained by the slide agglutination method. The superscript notation "c" indicates that the strain had been obtained from the Institute of Medical Science, the University of Tokyo. The symbol "nt" indicates non-encapsulated type. In addition, in FIG. 16, the superscript notation "a" indicates that the strain had been obtained from Department of Microbiology, Nihon University School of Dentistry. The superscript notation "b" indicates that the strain had been obtained from Department of Microbiology, Gifu University School of Medicine. The superscript notation "c" indicates that the strain had been obtained from the Institute of Medical Science, the University of Tokyo.

Figure 17:
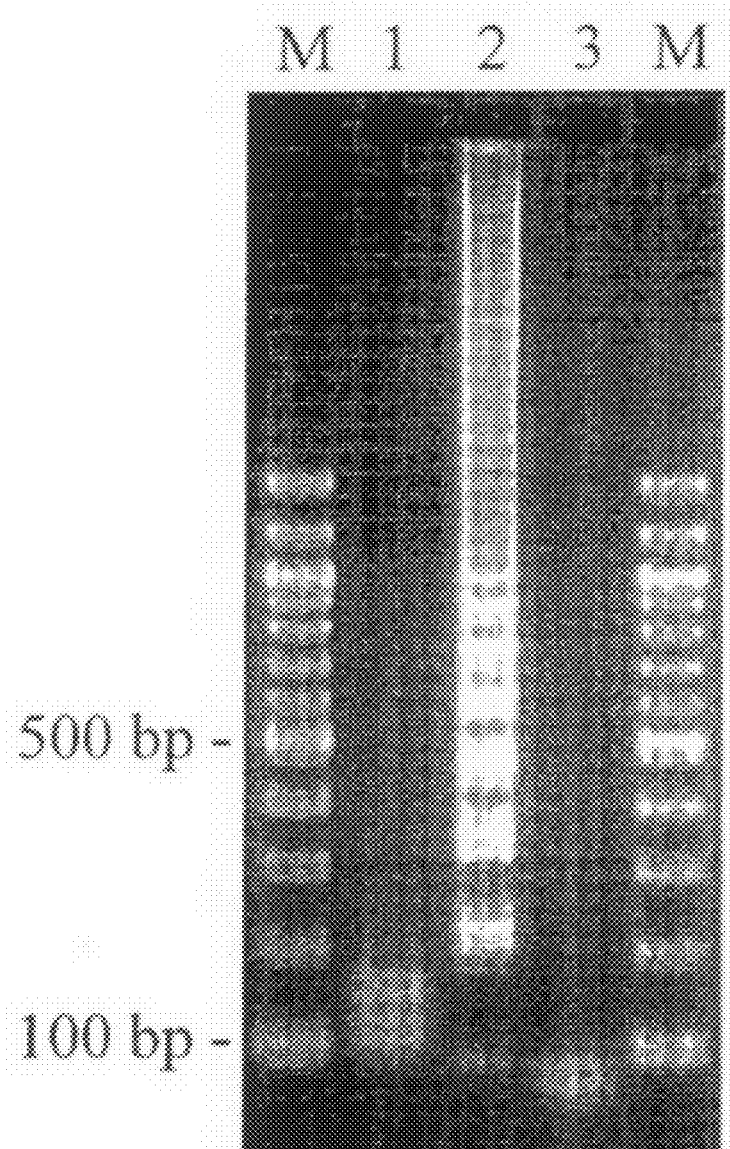
FIG. 17 is a photograph of the gel obtained by electrophoresing an amplified product obtained after a LAMP reaction (Example 11).

As a result, as shown in FIGS. 15 and 16, when all strains of Hib, including clinically isolated strains, were used as templates, even if any one of the LAMP primer sets of Examples 11 to 19 was used, the presence of an amplified product was confirmed after completion of the incubation for 60 minutes. In contrast, in the case of all other strains, including strains of *H. influenzae* having different capsular serotypes, after completion of the incubation for 60 minutes, no amplified products were confirmed. FIG. 17 shows the results obtained by performing electrophoresis on the amplified product, which had been obtained using Hib as a template. In FIG. 17, lane M on the left side is a lane obtained by feeding a marker for indicating intervals of 100 bp. Lane 1 is a lane obtained by treating the amplified product of lane 2 with Hpy1881 and then electrophoresing the resultant. Lane 2 is a lane obtained by electrophoresing an amplified product obtained when the template DNA concentration was set at 106 copies. Lane 3 is a lane obtained by electrophoresing an amplified product obtained when the template DNA concentration was set at 0 copy. In the case of lane 2, the amplified product had a ladder electrophoretic pattern. It was thereby confirmed that the amplified product had an inversed portion, and that it adopted a stem-loop structure characteristic of the LAMP reaction. In addition, the sections of 125 bp and 135 bp of Example 11 had appeared in lane 1, and thus it was confirmed that a portion to be targeted had been amplified. Moreover, the amplified product was also subjected to sequencing analysis. As a result, the sequence amplified as a result of the LAMP reaction matched with an anticipated sequence.

On the other hand, in the case of detection according to the slide agglutination method, a majority of Hib strains were detected, but one type of Hib strain was not detected. The reason why one type of Hib strain was not detected is considered that the expression level of capsule was low. However, in detection of Hib, the greatest risk is detection failure. In the case of detection using phenotype, such a risk is inevitable.

From these results, it was confirmed that the method of detecting Hib of the present embodiment has high specificity and is excellent in terms of detection reliability.

(Concerning Sensitivity Confirmation Test)

Next, detection sensitivity was obtained using each of the primer sets of the aforementioned Examples 11 and 14 to 19. Such detection sensitivity will be described below.

(1) Preparation of Chromosomal DNA

In the present test, as in the case of the specificity confirmation test, chromosomal DNA was purified from *H. influenzae* IID984, and it was then used as a template. The template DNA concentration (copy number) in the reaction solution was assayed, at a molecular size of 1.9 Mbp, using Ultrospec 3300 Pro spectrophotometer.

(2) Concerning LAMP Reaction

The template DNA solution, which had previously been assayed as described in (1) above, was diluted with a stepwise of 10 times, so as to prepare a solution that was diluted by a factor between 1 and 1,000,000. Using this solution as a template DNA solution for the LAMP reaction, a detection limit was confirmed. It is to be noted that the LAMP reaction solution was the same as that used in the aforementioned specificity confirmation test in terms of the additive amount of the template DNA solution and the additive amounts of other additives, with the exception that the concentration of the template DNA solution was different. In addition, with regard to the LAMP reaction, the reaction solution was incubated at 63° C. for 35 minutes or 60 minutes, so as to promote the reaction. Finally, the reaction solution was heated at 80° C. for 2 minutes, so as to terminate the reaction.

Moreover, in order to compare with the detection method of the present invention, amplification and detection were carried out also by the PCR method (Comparative example 11). At the time, the same template DNA solution as that used in the LAMP reaction was used as a template DNA solution for the PCR reaction, so as to confirm a detection limit. As PCR primers, the primers described in the aforementioned Non-Patent Document 1 were used (SEQ ID NOS: 80 to 82). The PCR reaction solution (10 µl) was prepared by mixing deoxynucleoside triphosphate (0.2 mM each), Tris-HCl buffer (10 mM; pH 8.3), KCl (50 mM), $MgCl_2$ (2 mM), 1 U ExTaq DNA polymerase (manufactured by TAKARA BIO INC.), primers (each 0.5 µM), and 1 µl of a template DNA solution.

The PCR reaction was carried out for 25 cycles using Thermal Cycler (manufactured by MJ Research). In each cycle, denaturation at 94° C. for 1 minute, annealing at 60° C. for 1 minute, and synthesis at 72° C. for 1 minute were successively carried out. Finally, heating at 72° C. for 10 minutes was carried out, so as to terminate the reaction.

(3) Concerning Confirmation of Presence or Absence of Amplification

With regard to the presence or absence of amplification as a result of the LAMP reaction, turbidity was measured using Loopamp (registered trade mark) real-time turbidity measurement apparatus (manufactured by TERAMECS Co., Ltd.; Model: LA-200). When the turbidity was 0.1 or greater, it was determined that amplification had been carried out.

Moreover, as with the aforementioned specificity confirmation test, the presence or absence of white turbidity was confirmed by visual observation, and it was also confirmed by electrophoresis.

Furthermore, the presence or absence of an amplified product generated as a result of PCR in Comparative examples was also confirmed by subjecting the amplified product (2 µl) to 3% agarose gel electrophoresis.

(4) Concerning Test Results

With regard to the test results, "+" indicates a case where an amplified product was confirmed as described above, and "−" indicates a case where such amplification was not confirmed. The test results are shown in FIG. 18.

As shown in FIG. 18, all the primer sets of Examples 11 and 14 to 19 exhibited sensitivity that was equivalent to or higher than the case of using PCR primers. In particular, the primer sets of Examples 11 and 16 to 18 had excellent sensitivity. It was confirmed that the primer set of Example 11 was particularly excellent in terms of sensitivity such that it had sensitivity that was 10,000 times higher than that of Comparative example 11 in which PCR primers were used. In Example 1, even in the case of incubation for 35 minutes, 1 copy of template could be detected, and thus it was confirmed that the primer set of Example 1 is extremely excellent in terms of sensitivity and promptness.

(Concerning Real-Time Turbidity Measurement Test)

(1) Concerning Detection Promptness

A test to confirm the detection promptness of the primer sets of Examples 11 to 19 was carried out. In the present test, the template DNA concentration was set at $10^6$ copies, and each primer set was added thereto. Thereafter, the composition of the LAMP reaction solution and conditions for the LAMP reaction were determined to be the same as those as described above, and the LAMP reaction was then carried out. During the reaction, using the aforementioned real-time turbidity measurement apparatus, the absorbance at 650 nm was read out every 6 seconds, and the threshold time was then measured.

Figure 19:
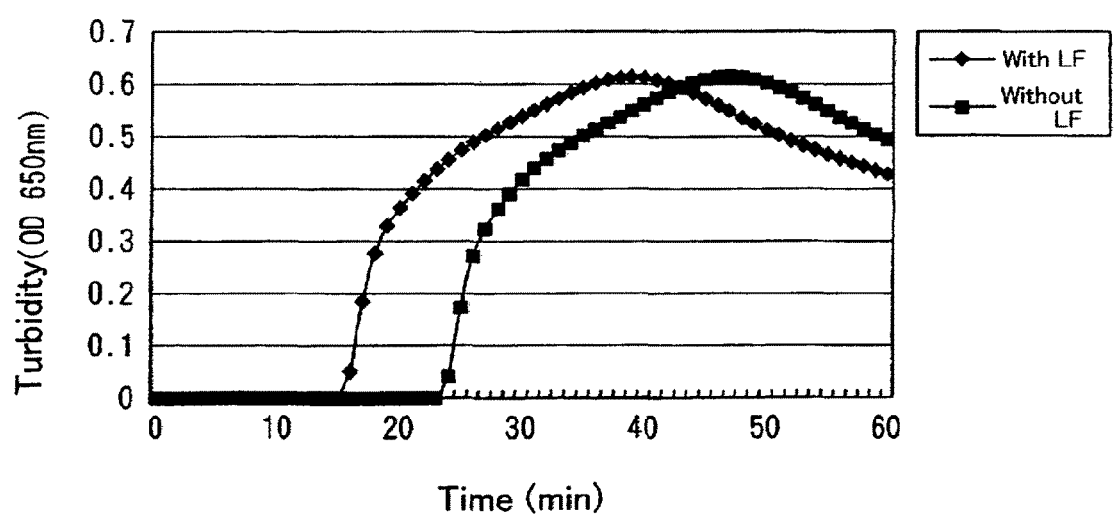
FIG. 19 is a graph showing the effect of determining Loop primers in Example 11.

The results are shown in FIG. 14. As shown in FIG. 14, the threshold times of all the examples were relatively short. In particular, the primer set of Example 11 had an extremely short threshold time when compared with other examples, and thus it was confirmed that the primer set of Example 11 was able to significantly rapidly detect Hib. In addition, with regard to the primer set of Example 11, a test was carried out to confirm a difference in the LAMP reaction between the case of addition of LF and the case of non-addition of LF. The test results are shown in FIG. 19. As shown in FIG. 19, it was confirmed that addition of LF reduces the threshold time from 25 minutes to 16 minutes.

Figure 20:
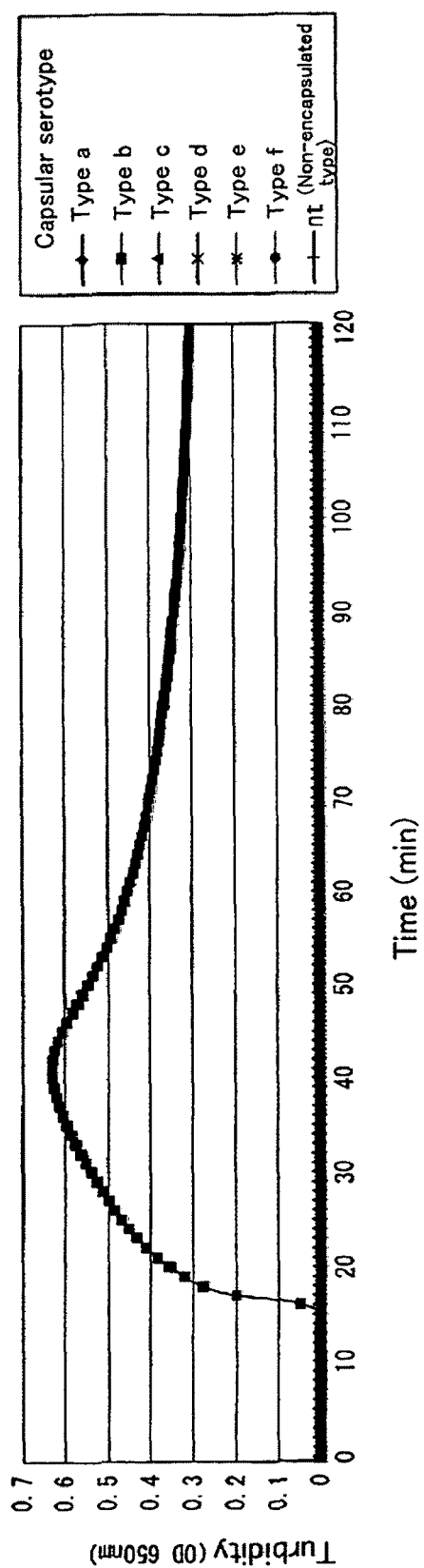
FIG. 20 is a graph showing the results obtained by carrying out a LAMP reaction for 120 minutes using the DNA of each of *H. influenzae* strains of capsular serotypes a to f and of non-encapsulated type as a template in Example 11.

Moreover, FIG. 20 shows a change in the turbidity obtained when the LAMP reaction was carried out for 120 minutes using each of *H. influenzae* strains of capsular serotypes a to f and non-encapsulated type as a template in Example 11. As shown in FIG. 20, even when the reaction was carried out for 120 minutes, no amplified products were generated other than the case where Hib was used as a template. The same tendency was confirmed in terms of Examples 12 and 13 (not shown in the figure). In a clinical test, it is assumed that a certain period of time after the threshold time of each primer set has passed, white turbidity is observed. In the case of the primer sets of Examples 11 to 13, since reliable results can be obtained even after a long period of time has passed after such threshold time, these primer sets can easily be used in clinical sites.

(2) Concerning Quantitative Capability

Next, the following test was carried out on Example 11 that is excellent in terms of specificity, sensitivity, and promptness. First, the template DNA copy number was adjusted to be 0 to $10^6$ per reaction tube, and the LAMP primer set of Example 111 was added thereto. Thereafter, the composition of the LAMP reaction solution and conditions for the LAMP reaction were determined to be the same as those as described above, and the LAMP reaction was then carried out. During the reaction, using the aforementioned real-time turbidity measurement apparatus, the absorbance at 650 nm was read out every 6 seconds.

Figure 21:
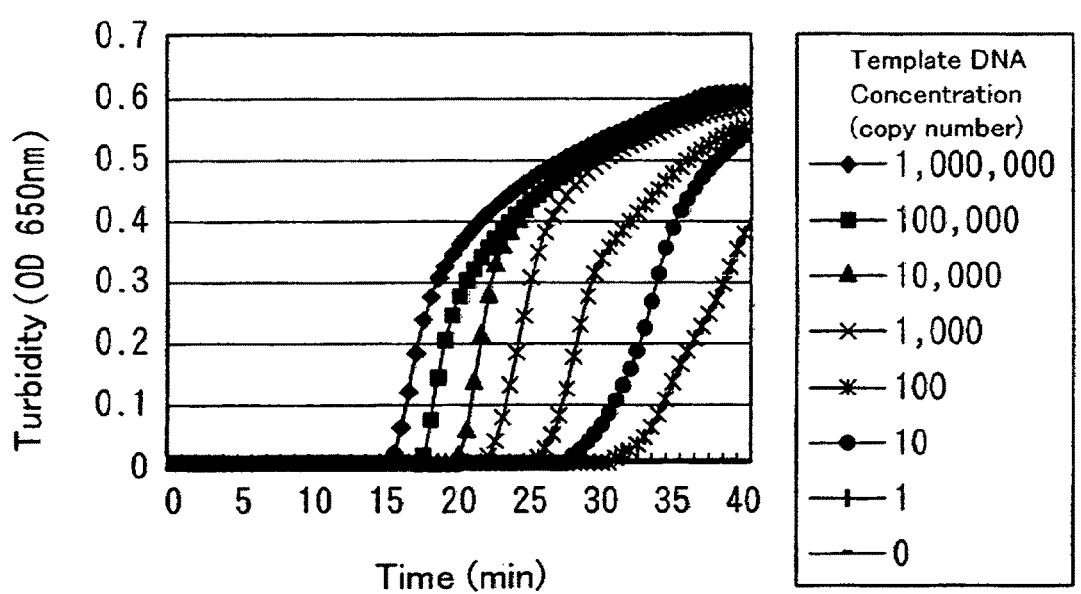
FIG. 21 is a graph showing the results of the real-time turbidity measurement of Example 11.

As a result, as shown in FIG. 21, it was confirmed that when the copy number of template DNA is 1 copy or greater, the turbidity becomes 0.1 or greater within 60 minutes. Such results correspond to the results regarding the presence or absence of amplification obtained by visual observation and electrophoresis in the aforementioned sensitivity test. Moreover, it was also confirmed that as the initial amount of template DNA increases, the threshold time becomes shorter.

Figure 22:
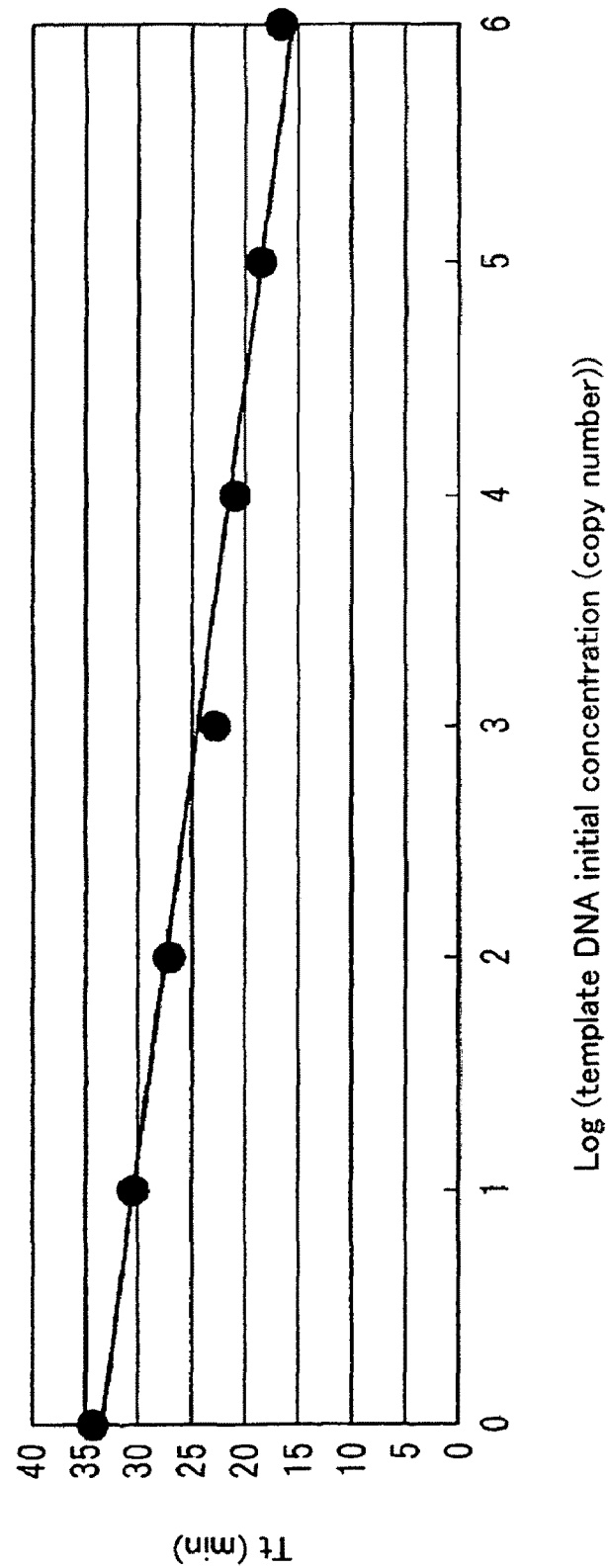
FIG. 22 is a graph showing the relationship between the turbidity as shown in FIG. 21 and the common logarithm of the amount of template DNA.

FIG. 22 shows the relationship between the threshold time in the case of Example 11 and the common logarithm of the initial amount of template DNA. Linearity was observed between such two factors, and a high correlation (correlation coefficient $r^2=0.979$) was obtained. From these results, it was confirmed that the primer set of Example 11 has excellent quantitative capability, as described above.

As stated above, when the detection method of the present embodiment is compared with the conventional PCR method, since the LAMP reaction progresses under isothermal conditions and the results can be confirmed by visual observation, Hib can be simply, rapidly and accurately detected, even in hospital with simple facility. Moreover, since the detection method of the present embodiment is extremely excellent in terms of sensitivity, it enables early diagnosis of infection and early treatment thereof. Furthermore, the detection method of the present embodiment also enables assay.

INDUSTRIAL APPLICABILITY

According to the method of detecting *Haemophilus influenzae* of the present invention, it is possible to accurately detect *H. influenzae*, and particularly to detect *H. influenzae* by distinguishing it from *H. parainfluenzae* (FIG. 23 (A)). In addition, according to the method of detecting Hib of the present invention, it is possible to simply, rapidly, and accurately detect Hib, by distinguishing it from other capsular serotype and non-encapsulated type *H. influenzae* (FIG. 23 (B)).

SEQUENCE LISTING FREE TEXT

SEQ ID NO: 12 P6 protein gene

SEQ ID NO: 13 Synthetic DNA (Comparative example 1)

SEQ ID NO: 14 Synthetic DNA (Comparative example 1)

SEQ ID NO: 79 Capsulation locus region II of Hib

SEQ ID NO: 80 Synthetic DNA (Comparative example 11)

SEQ ID NO: 81 Synthetic DNA (Comparative example 11)

SEQ ID NO: 82 Synthetic DNA (Comparative example 11)

the nucleotide sequences as described in (c) above;

(e) 4 types of primers each having a nucleotide sequence that is identical to or substantially identical to each of the nucleotide sequences as shown in SEQ ID NOS: 7 to 9 and 11;

(f) 4 types of primers each having a nucleotide sequence that is complementary to each of the nucleotide sequences as described in (e) above;

(g) 4 types of primers each having a nucleotide sequence that is identical to or substantially identical to each of the nucleotide sequences as shown in SEQ ID NOS: 15 to 18;

(h) 4 types of primers each having a nucleotide sequence that is complementary to each of the nucleotide sequences as described in (g) above;

(i) 4 types of primers each having a nucleotide sequence that is identical to or substantially identical to each of the nucleotide sequences as shown in SEQ ID NOS: 20 to 23;

(j) 4 types of primers each having a nucleotide sequence that is complementary to each of the nucleotide sequences as described in (i) above;

(k) 4 types of primers each having a nucleotide sequence that is identical to or substantially identical to each of the nucleotide sequences as shown in SEQ ID NOS: 24 to 27;

(l) 4 types of primers each having a nucleotide sequence that is complementary to each of the nucleotide sequences as described in (k) above;

(m) 4 types of primers each having a nucleotide sequence that is identical to or substantially identical to each of the nucleotide sequences as shown in SEQ ID NOS: 26 and 28 to 30;

(n) 4 types of primers each having a nucleotide sequence that is complementary to each of the nucleotide sequences as described in (m) above;

(o) 4 types of primers each having a nucleotide sequence that is identical to or substantially identical to each of the nucleotide sequences as shown in SEQ ID NOS: 26 and 30 to 32;

(p) 4 types of primers each having a nucleotide sequence that is complementary to each of the nucleotide sequences as described in (o) above;

(q) 4 types of primers each having a nucleotide sequence that is identical to or substantially identical to each of the nucleotide sequences as shown in SEQ ID NOS: 33 to 36; and (r) 4 types of primers each having a nucleotide sequence that is complementary to each of the nucleotide sequences as described in (q) above.

3. The method of detecting *Haemophilus influenzae* according to claim 2, which is characterized in that said LAMP primer set is any one of LAMP primer sets comprising the primers as described in the following (s) to (x):

(s) the 4 types of primers according to claim 2(a), and a primer having a nucleotide sequence that is identical to or substantially identical to the nucleotide sequence as shown in SEQ ID NO: 5 in the sequence listing;

(t) the 4 types of primers according to claim 2(b), and a primer having a nucleotide sequence that is identical to or substantially identical to a nucleotide sequence complementary to the nucleotide sequence as shown in SEQ ID NO: 5 in the sequence listing;

(u) the 4 types of primers according to claim 2(c), and a primer having a nucleotide sequence that is identical to or substantially identical to the nucleotide sequence as shown in SEQ ID NO: 10 in the sequence listing;

(v) the 4 types of primers according to claim 2(d), and a primer having a nucleotide sequence that is identical to or substantially identical to a nucleotide sequence complementary to the nucleotide sequence as shown in SEQ ID NO: 10 in the sequence listing;

(w) the 4 types of primers according to claim 2(g), and a primer having a nucleotide sequence that is identical to or substantially identical to the nucleotide sequence as shown in SEQ ID NO: 19 in the sequence listing; and (x) the 4 types of primers according to claim 2(h), and a primer having a nucleotide sequence that is identical to or substantially identical to a nucleotide sequence complementary to the nucleotide sequence as shown in SEQ ID NO: 19 in the sequence listing.

4. A method of detecting *Haemophilus influenzae* Type b based on the presence or absence of nucleic acid amplification as a result of a nucleic acid amplification reaction using a primer set, which is characterized in that a LAMP primer set is used as said primer set, wherein all primers have a nucleotide sequence that is identical to or complementary to a partial nucleotide sequence in the region ranging from bp 1 to 6653 of the capsulation locus region II of the *Haemophilus influenzae* Type b.

5. The method of detecting *Haemophilus influenzae* according to claim 4, which is characterized in that a LAMP primer set is used as said LAMP primer set, wherein all primers have a nucleotide sequence that is identical to or complementary to a partial nucleotide sequence in the region ranging from bp 5,000 to 6,653 of said capsulation locus region II.

6. The method of detecting *Haemophilus influenzae* according to claim 5, which is characterized in that said LAMP primer set is any one of LAMP primer sets comprising the primers as described in the following (A) to (R):

(A) 4 types of primers each having a nucleotide sequence that is identical to or substantially identical to each of the nucleotide sequences as shown in SEQ ID NOS: 43 to 46 in the sequence listing;

(B) 4 types of primers each having a nucleotide sequence that is complementary to each of the nucleotide sequences as described in (A) above;

(C) 4 types of primers each having a nucleotide sequence that is identical to or substantially identical to each of the nucleotide sequences as shown in SEQ ID NOS: 48 to 51;

(D) 4 types of primers each having a nucleotide sequence that is complementary to each of the nucleotide sequences as described in (C) above;

(E) 4 types of primers each having a nucleotide sequence that is identical to or substantially identical to each of the nucleotide sequences as shown in SEQ ID NOS: 53 to 56;

(F) 4 types of primers each having a nucleotide sequence that is complementary to each of the nucleotide sequences as described in (E) above;

(G) 4 types of primers each having a nucleotide sequence that is identical to or substantially identical to each of the nucleotide sequences as shown in SEQ ID NOS: 58 to 61;

(H) 4 types of primers each having a nucleotide sequence that is complementary to each of the nucleotide sequences as described in (G) above;

(I) 4 types of primers each having a nucleotide sequence that is identical to or substantially identical to each of the nucleotide sequences as shown in SEQ ID NOS: 62 to 65;

(J) 4 types of primers each having a nucleotide sequence that is complementary to each of the nucleotide sequences as described in (I) above;

(K) 4 types of primers each having a nucleotide sequence that is identical to or substantially identical to each of the nucleotide sequences as shown in SEQ ID NOS: 67 to 70;

(L) 4 types of primers each having a nucleotide sequence that is complementary to each of the nucleotide sequences as described in (K) above;

(M) 4 types of primers each having a nucleotide sequence that is identical to or substantially identical to each of the nucleotide sequences as shown in SEQ ID NOS: 71 to 74;

(N) 4 types of primers each having a nucleotide sequence that is complementary to each of the nucleotide sequences as described in (M) above;

(O) 4 types of primers each having a nucleotide sequence that is identical to or substantially identical to each of the nucleotide sequences as shown in SEQ ID NOS: 73 to 76;

(P) 4 types of primers each having a nucleotide sequence that is complementary to each of the nucleotide sequences as described in (O) above;

(O) 4 types of primers each having a nucleotide sequence that is identical to or substantially identical to each of the nucleotide sequences as shown in SEQ ID NOS: 73, 74, 77, and 78; and (R) 4 types of primers each having a nucleotide sequence that is complementary to each of the nucleotide sequences as described in (O) above.

7. The method of detecting *Haemophilus influenzae* according to claim 6, which is characterized in that said LAMP primer set is any one of LAMP primer sets comprising the primers as described in the following (S) to (Z):

(S) the 4 types of primers according to claim 6(A), and a primer having a nucleotide sequence that is identical to or substantially identical to the nucleotide sequence as shown in SEQ ID NO: 47 in the sequence listing;

(T) the 4 types of primers according to claim 6(B), and a primer having a nucleotide sequence that is identical to or substantially identical to a nucleotide sequence complementary to the nucleotide sequence as shown in SEQ ID NO: 47 in the sequence listing;

(U) the 4 types of primers according to claim 6(C), and a primer having a nucleotide sequence that is identical to or substantially identical to the nucleotide sequence as shown in SEQ ID NO: 52 in the sequence listing;

(V) the 4 types of primers according to claim 6(D), and a primer having a nucleotide sequence that is identical to or substantially identical to a nucleotide sequence complementary to the nucleotide sequence as shown in SEQ ID NO: 52 in the sequence listing;

(W) the 4 types of primers according to claim 6(E), and a primer having a nucleotide sequence that is identical to or substantially identical to the nucleotide sequence as shown in SEQ ID NO: 57 in the sequence listing;

(X) the 4 types of primers according to claim 6(F), and a primer having a nucleotide sequence that is identical to or substantially identical to a nucleotide sequence complementary to the nucleotide sequence as shown in SEQ ID NO: 57 in the sequence listing;

(Y) the 4 types of primers according to claim 6(I), and a primer having a nucleotide sequence that is identical to or substantially identical to the nucleotide sequence as shown in SEQ ID NO: 66 in the sequence listing; and (Z) the 4 types of primers according to claim 6(J), and a primer having a nucleotide sequence that is identical to or substantially identical to a nucleotide sequence complementary to the nucleotide sequence as shown in SEQ ID NO: 66 in the sequence listing.

8. A primer set for detecting *Haemophilus influenzae*, which is characterized in that it is any one of the LAMP primer sets according to claims 1 to 7.

9. A kit for detecting *Haemophilus influenzae*, which is characterized in that it comprises the LAMP primer sets according to claims 1 to 7.

---

What is claimed is:

1. A method of detecting *Haemophilus influenzae* Type b comprising
   detecting the presence or absence of nucleic acid amplification as a result of a nucleic acid amplification reaction using a LAMP primer set,
   wherein said primer set comprises the primers as described in the following (A) or (B):
   (A) 4 types of primers each having a nucleotide sequence that is identical to each of the nucleotide sequences as shown in SEQ ID NOS: 43 to 46 in the sequence listing; or
   (B) 4 types of primers each having a nucleotide sequence that is fully complementary to each of the nucleotide sequences as described in (A) above.

2. The method of detecting *Haemophilus influenzae* Type b according to claim 1, wherein said primer set comprises the primers as described in the following (S) or (T):
   (S) the 4 types of primers according to claim 1(A), and a primer having a nucleotide sequence that is identical to the nucleotide sequence as shown in SEQ ID NO: 47 in the sequence listing; or
   (T) the 4 types of primers according to claim 1(B), and a primer having a nucleotide sequence that is identical to a nucleotide sequence fully complementary to the nucleotide sequence as shown in SEQ ID NO: 47 in the sequence listing.

3. A primer set for detecting *Haemophilus influenzae* Type b, comprising the primer set as described in the following (A) or (B):
   (A) 4 types of primers each having a nucleotide sequence that is identical to each of the nucleotide sequences as shown in SEQ ID NOS: 43 to 46 in the sequence listing; or
   (B) 4 types of primers each having a nucleotide sequence that is fully complementary to each of the nucleotide sequences as described in (A) above.

4. A kit for detecting *Haemophilia influenzae* Type b, comprising the primer set as described in the following (A) or (B):
   (A) 4 types of primers each having a nucleotide sequence that is identical to each of the nucleotide sequences as shown in SEQ ID NOS: 43 to 46 in the sequence listing; or
   (B) 4 types of primers each having a nucleotide sequence that is fully complementary to each of the nucleotide sequences as described in (A) above.

5. A primer set for detecting *Haemophilus influenzae* Type b of claim 3, comprising the primer set as described in the following (S) or (T):
   (S) the 4 types of primers according to claim 3(A), and a primer having a nucleotide sequence that is identical to the nucleotide sequence as shown in SEQ ID NO: 47 in the sequence listing; or
   (T) the 4 types of primers according to 8(B), and a primer having a nucleotide sequence that is identical to a nucleotide sequence fully complementary to the nucleotide sequence as shown in SEQ ID NO: 47 in the sequence listing.

6. A kit for detecting *Haemophilus influenzae* Type b according to claim 4, comprising the primer set as described in the following (S) or (T):
   (S) the 4 types of primers according to claim 4(A), and a primer having a nucleotide sequence that is identical to the nucleotide sequence as shown in SEQ ID NO: 47 in the sequence listing; or
   (T) the 4 types of primers according to 9(B), and a primer having a nucleotide sequence that is identical to a nucleotide sequence fully complementary to the nucleotide sequence as shown in SEQ ID NO: 47 in the sequence listing.

* * * * *

SEQUENCE LISTING

```
<160> NUMBER OF SEQ ID NOS: 83

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
acacctttac cagctaaata acctttggta caccagaata caacatc                    47

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
aggcacagta tcttacggtg aatatgcagc ttcatcatga cc                         42

<210> SEQ ID NO 3
<211> LENGTH: 22
<212> TYPE: DNA
<213> ORGANISM: Artificial Sequence
<220> FEATURE:
```

<223> OTHER INFORMATION: Description of Artificial Sequence:synthetic
      DNA

<400> SEQUENCE: 3
tagaaggtaa cactgatgaa cg                                              22

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
tacgctaaca ctgcacga                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
tgcacgacgt tggcctaa                                                   18

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
cagcatcaac acctttacca gcacaacatc gcattaggcc                           40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7
ggcacagtat cttacggtga aggcagcttc atcatgacct                           40

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 8
gaacgtggta caccagaa                                                   18

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence:synthetic

DNA

<400> SEQUENCE: 9
cactgcacga cggttt                                          16

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 10
cctttaactg catctgcacg acg                                  23

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 11
ccagcatcaa cacctttacc agctaacaac atcgcattag gcc            43

<210> SEQ ID NO 12
<211> LENGTH: 462
<212> TYPE: DNA
<213> ORGANISM: Haemophilus influenzae

<400> SEQUENCE: 12
atgaacaaat tgttaaaatc attattagtt gcaggttctg tagctgcatt agcagcttgt    60
agttcatcta acaacgatgc tgcaggcaat ggtgctgctc aaacttttgg cggttactct   120
gttgctgatc ttcaacaacg ttacaatacc gtttatttcg gttttgataa atatgacatt   180
actggtgaat acgttcaaat cttagacgcg cacgctgcat atttaaatgc aacgccagct   240
gctaaagtat tagtagaagg taacactgat gaacgtggta caccagaata caacatcgca   300
ttaggccaac gtcgtgcaga tgcagttaaa ggttatttag ctggtaaagg tgttgatgct   360
ggtaaattag gcacagtatc ttacggtgaa gaaaaacctg cagtattagg tcatgatgaa   420
gctgcatatt ctaaaaaccg tcgtgcagtg ttagcgtact aa                      462

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 13
aacttttggc ggttactctg                                      20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 14
ctaacactgc acgacggttt                                              20

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 15
tgcgatgttg tattctggtg tgctgctaaa gtattagtag aagg                   44

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 16
ccaacgtcgt gcagatgcgc ctaatttacc agcatcaa                          38

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 17
gcatatttaa atgcaacgcc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 18 caggttttc ttcaccgtaa                                               20

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 19
aaaggttatt tagctggtaa aggtg                                        25

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 20

```
gcgtctaaga tttgaacgta ttcaccttca acaacgttac aataccg              47
```

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 21

```
caacgccagc tgctaaagta gatgttgtat tctggtgtac c                    41
```

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 22

```
tgctgctcaa acttttgg                                              18
```

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 23

```
taactgcatc tgcacgac                                              18
```

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 24

```
cgcgtctaag atttgaacgt caacaacgtt acaataccg                       39
```

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 25

```
gccagctgct aaagtattag tagaaggcgt tggcctaatg cgatg                45
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 26

```
ggttactctg ttgctgatct                                            20
```

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 27
ttaactgcat ctgcacga                                                   18

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 28
cgcgtctaag atttgaacgt attcatcaac aacgttacaa taccg                     45

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 29
caacgccagc tgctaaagta gatgttgtat tctggtgtac c                         41

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 30
cgacgttggc ctaatgc                                                    17

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 31
gcgcgtctaa gatttgaacg tattctcaac aacgttacaa taccg                     45

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 32
caacgccagc tgctaaagta tgatgttgta ttctggtgta cc                        42

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 33
gtgtaccacg ttcatcagtg tttttaaatg caacgccagc                    40

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 34
acatcgcatt aggccaacgt gcctaattta ccagcatcaa c                  41

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 35
cgttcaaatc ttagacgcg                                           19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 36
gcaggttttt cttcaccgta                                          20

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 37
ccaaaagttt gagcagcacc atagcagctt gtagttcatc t                  41

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 38
cggttactct gttgctgatc ttcaacgtat tcaccagtaa tgtca             45

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 39
agttgcaggt tctgtagc                                                   18

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 40
gcatttaaat atgcagcgtg                                                 20

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 41
cgccaaaagt ttgagcagca cagcagcttg tagttcatct                           40

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 42
ctgttgctga tcttcaacaa cgtgatttga acgtattcac cagt                      44

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 43
acttctttac caaaggcatc atttttgcgt tgttgaatt ctgg                       44

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 44
ctgatgatat gggtacatct gttcgcgaag aatgagaagt tttgtgg                   47

<210> SEQ ID NO 45

```
<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 45
cgccaataca ttcaacaaga                                                 20

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 46
cgtatggggt ttgtgca                                                    17

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 47
gcagacgacc aaaggtatct tg                                              22

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 48
tgtgcaaaaa taggctcgaa gaacttcatc ttagcaccac aa                        42

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 49
ccccatacga cagtattcct gattcgctta cgcttctatc tcg                       43

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 50
ggtacatctg ttcgccata                                                  19

<210> SEQ ID NO 51
<211> LENGTH: 20
```

-continued

<212> TYPE: DNA
<213> ORGANISM: Artificial Sequence
<220> FEATURE:
<223> OTHER INFORMATION: Description of Artificial Sequence:synthetic
      DNA

<400> SEQUENCE: 51
ataacccttc cgaaatgaga                                              20

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 52
ggtttgtgca aaataggct cga                                           23

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 53
tgtgcaaaaa taggctcgaa gaacttcatc ttagcaccac aa                     42

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 54
ccccatacga cagtattcct gattcgctta cgcttctatc tcg                    43

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 55
ggtacatctg ttcgccata                                               19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 56
ataacccttc cgaaatgaga                                              20

<210> SEQ ID NO 57
<211> LENGTH: 25
<212> TYPE: DNA

<213> ORGANISM: Artificial Sequence
<220> FEATURE:
<223> OTHER INFORMATION: Description of Artificial Sequence:synthetic
    DNA

<400> SEQUENCE: 57
ggttcaattc tgcctttttc ttcgt                                              25

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 58
ggtaaccatt cttcagagat ggctgcaaaa gcagctgtgg                              40

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 59
caccaatgag aaccaaggca ttcgacaaga gaggcaaaag ct                           42

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 60
gccgtccatt ctatgctat                                                     19

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 61
gatgttaccc gtctcgc                                                       17

<210> SEQ ID NO 62
<211> LENGTH: 41
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 62
ccagcctcaa catcatattg agagccggca tagatcgctt g                            41

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence:synthetic
DNA

<400> SEQUENCE: 63
tatcggaaaa accggtctag accctatgcc accttcccat g          41

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:synthetic
DNA

<400> SEQUENCE: 64
gatcatgtta ttaccgcagg          20

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence:synthetic
DNA

<400> SEQUENCE: 65
tgccctacat aagacaagc          19

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:synthetic
DNA

<400> SEQUENCE: 66
acaggtaaag gcattcccgc          20

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence:synthetic
DNA

<400> SEQUENCE: 67
tgttctatgc caccttccca tacacaggta aaggcattcc          40

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence:synthetic
DNA

<400> SEQUENCE: 68
ggcaagtaac aaacaccttg ctcggatgtg gtcgaataac g          41

<210> SEQ ID NO 69
<211> LENGTH: 20
<212> TYPE: DNA
<213> ORGANISM: Artificial Sequence
<220> FEATURE:

<223> OTHER INFORMATION: Description of Artificial Sequence:synthetic
      DNA

<400> SEQUENCE: 69
gggcgatact tttatcggaa                                                   20

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 70
ttttgcagac gatgtcct                                                     18

<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 71
ccagttgatt tttggtagcc aatcgatcgt gcggatactc gt                          42

<210> SEQ ID NO 72
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 72
ttaccaatat agccgttgga cacacaacag aaccatcagc gtg                         43

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 73
gtacttgcct gaagacgt                                                     18

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 74
gcagtttgaa taccaagacg                                                   20

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence:synthetic

```
                         DNA

<400> SEQUENCE: 75
ccagttgatt tttggtagcc aatcgaatgt tagatcgtgc gga                       43

<210> SEQ ID NO 76
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 76
ttaccaatat agccgttgga cacacgaaca gaaccatcag cgt                       43

<210> SEQ ID NO 77
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 77
cccagttgat ttttggtagc catcgtgcgg atactcgt                             38

<210> SEQ ID NO 78
<211> LENGTH: 41
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 78
taccaatata gccgttggac acacacagaa ccatcagcgt g                         41

<210> SEQ ID NO 79
<211> LENGTH: 8640
<212> TYPE: DNA
<213> ORGANISM: Haemophilus influenzae

<400> SEQUENCE: 79
tttctcattg atttatcatc tcacaagtaa ggaatacaag tgcttaaatt tgcaaatcgg      60
cttgcaatcc accacacctc tatgcgtaaa cacagtcgga agagtatagc atttattcta     120
aaggggaaaa atattattca ctgtgactgt ctttatacaa attatatact tcgaaaaatt     180
atgcaatata atatttctaa ataatcaagg ttaacatttt aacacccatc tataagaaaa     240
atgatataat tgcaagaatg gatagcaggg ttattcatta aatgttaaaa ataaagtaga     300
tttttgaatt tcccttgaaa aaacgtgtat gtttggctac atttttgcct ataaaaaacc     360
aaaatagttg ggtgtttaac attgtttcta ctcttaccta aacgtatttc caattaatct     420
ctggagaatt aatatgaata aaaataaaaa cataggaatc attctagctg gtggtgttgg     480
ctctcgtatg ggattgggct acccaaaaca attctcaaaa attgcaggca aaactgcgct     540
ggagcatact cttgccattt tccaagaaca taaagaaatt gatgaaatta tcatcgtttc     600
tgagcgtacc tcttatcgtc gtattgaaga tatcgtatca aagctggatt tttccaaagt     660
taatcgtatt attttggtg gtaaagaacg ctctgattct actctttctg caatcacagc     720
tcttcaagat gaaccagaaa atacgaaatt aatcattcat gatgctgtac gacctttact     780
```

```
agcgactgag ataatctctg aatgtattgc gaaattagat aagtacaatg ctgtagatgt    840
ggctattcct gcagttgata ccattgttca tgttaataat gatacccaag aaattattaa    900
aattcctaag cgtgctgaat actaccaagg ccaaactcca caagcattta aactaggcac    960
gctaaaaaaa gcttacgata tttatacaca aggtggcatc gaaggtactt gtgattgttc   1020
tattgtgtta aaaccctac ctgaagaaag agttggtatc gtttcaggtt ctgaaaccaa    1080
cattaaatta actcgcccag ttgatctttt tatcgctgat aaattattcc aaagccgtag   1140
tcatttttca ctacgtaata tcacctctat tgatcgccta tatgatatga aagatcaggt   1200
attagttgtt attggtggaa gctatggtat tggcgcgcat attatcgata ttgcaaaaaa   1260
atttggaatt aaaacatata gccttagtcg ttcaaatggt gtcgatgttg gtgatgttaa   1320
gtctattgaa aaagcattcg cagaaattta cgcaaaagaa cacaaaatag accatatcgt   1380
aaatactgct gcggtgttaa atcataaaac gttagtatca atgtcttatg aagaaatttt   1440
aactagtatc aatgtaaact acacgggcat gattaatgct gtgataacgg cttatcctta   1500
cttaaaacaa actcatggta gttttttagg tttcacatca agctcgtata cacgaggccg   1560
tccattctat gctatttact cttctgcaaa agcagctgtg gtaaacttaa ctcaagccat   1620
ctctgaagaa tggttaccgg ataatattaa aattaactgc gttaatccag agagaacaaa   1680
aacaccaatg agaaccaagg cattcggtat tgaacctgaa ggtacattac ttgatgctaa   1740
aacagtagct tttgcctctc ttgtcgtact tgctagccgc gagacgggta acatcattga   1800
tgttgtatta aaagatgaag aatatatatc caatatttta gctgatctct ataaataaac   1860
ttgagtaagt ctgttatggc tatcccccc tattttattt atttggacac caagattatt   1920
ggtgcggtaa agcaaacaat tactttttt gaacatggcg tgtttcctcg tgaaaacacg   1980 atcatttag taaaaagta taaacataag tccgctaaaa tcattgagcg agctttaaat   2040
aaagcttctc tcaactatca ttttgtgaat gctgcatatc ttgatgcatt gaaagaaggt   2100
gtaattttct acccatttaa tgcacaatct aattgtcgtg cagtagcaaa ccgtaacctt   2160
actcatattt ttattactca tggggaaagt aataaaatta cttcagttaa accgattgta   2220
cgtatttatg atcatgttat taccgcaggt aatgccggca tagatcgctt gattgctcat   2280
aaaatcttct ctcaatatga tgttgaggct ggaagaatta ttcctatggg cgatactttt   2340
atcggaaaaa ccggtctaga ccacacaggt aaaggcattc ccgccatctt ctatgtgcca   2400
acatgggaag gtggcataga acaagaaaac tattcaagct tgtcttatgt agggcaagta   2460
acaaacacct tgctcctatt aagtaaacac tatcaaatca atgaaatcgt tattcgacca   2520
catccgaata caggacatcg tctgcaaaat tatcatcaat ttttaatgga tattgtaaaa   2580
acacttttac ataaaggatt aaaggtgaca ttatataaac ctcatgtagg gcttacattc   2640
tcacaagctt ggaaactacg acgaaatggg ggtacattaa cttccgattt aagcaaattt   2700
tatgcaatta ttgggctttg tgatatttca gctagaaaa gtcaattatt aaatgaaaat   2760
attttctatt atttatttg ttcaaagca caaaagaat atttaattag tttaaaaaac   2820
agccaatact ataaaacaaa tactctcact tttggtgaga agctttattt tcaccatata   2880
tcaaaagacg atttttatca acttcgcaat tatatgatag aacaaaatta tttgaatatt   2940
ccacttaatc aacgaattga acaacttcta gcaaaattaa atcaattata aagtacatt    3000 ttattatgaa aacttggtta tttggctctt atgcttggca aggaaatcct aaggctttat   3060
tcctgtatat gcttgtaaat tgtaaagaaa cccacgaatg ctggtgggtt gcagacaacg   3120
aagaaagcat gaagagtata aaaaaatcta ctggcttaaa aaacattacg tttaccgata   3180
```

```
gtgaaaaagc taaagaactt ttccctcatg ccgacgttta cgtaacagaa aacttccgtg    3240
aaagttatcc agtttacatg aatgaaaata tcaaagtttt caacacatgg catggcgttg    3300
gtttaaaaca tattgaatta gcattaggca tgaattcagt attagctgaa agcattgttc    3360 gaaatatgt tcgaaactat gatatctaca aaaataatgt attgtttctt acaacatcgc     3420
aagcaatgga agatcacttc cttgaagata tggcgatcag taaagaacta attatccgcg    3480
ggaaataccc tcgcaatgca gtttatggtc ctaatgggat ccatacctat gatatcaata    3540
cgcttttacc aaaaaataaa agccaatata gccaaactat tcttttctgc ccaacttatc    3600
gtattggtgc aatccaaggt gttttaaata gcctattacc agattttgct aaacttgaag    3660
aagtttgccg tcataaaaat caactattca tcgttaaagt tcacccgttc atgaagaaag    3720
ataattactt cgctgaaatg agtgaaaaat ataaagatag tgaatacatc ctattttgga    3780
atgatgacta tgatatttat gaggcattca attctatcga tctcgcgatt attgactatt    3840
caagtatctt ttatgattta ttagatgctg gcgttgaaaa attcattcgt tatgtacctg    3900
acttagatga ataccagaat gatcttgagc taattggcga ttatgccgat ttaacagaag    3960
gtcgcatcgt taaatcattc caacaattat taaattgttt agataatgcc aacattaaaa    4020
tcatttcaac aaaaagaaaa caatatctta tggattattt ctttggattt aagaaagaaa    4080
ataaatcaat ggaatcttta attgcagatg ttgataattg ccaattacaa ccaaaatcgt    4140
taaaagaact ccatacattt gatattttg ataccttaat tcgccgctcg tcattacgtc     4200
catttagtat ttttgactat gtacgcgata agctaaagc atcaggtatc aaattcccgc     4260
ttgcattgac tgaaaattgg atcaatgtac gtaaccgtgc tgaacacgat gtgcgagata    4320
tcatgcgtaa acaacgtttt gagcgtcaat cagataaaat tgagattaca ttagacgata    4380
tctacactcg cttgcaaaaa aatctattac ttaccgatga acaaactgat ttcttaaaac    4440
aagctgaaat tgaagctgaa attgctcatg ttgagccaat tcaaaaacga attaactatc    4500
tcttctcgtt aaaagcgaaa ggacatgatg tagccatggc tagcgatatg tacttgcctg    4560
aagacgtaat ttataaaatg ttagatcgtg cggatactcg tttacgtgaa attccacttt    4620
atctttcaag tacgattggc taccaaaaat caactgggaa attataccaa cacatctttt    4680
tcgacttaga ttaccaatat agccgttgga cacactatgg cgataacaaa cacgctgatg    4740
gttctgttcc tcgccgtctt ggtattcaaa ctgcagtgca tgatattgat gatttttatcc    4800 catttgaaaa tgcaatggtt aatgcaatgg ataactataa ccgctatcca gcttaccagc    4860
ttgcaactaa gatgcatcgt taccgcacac agcttgttca agaaaatggt ttcggtaata    4920
ccctatttga aaccaaatat tacaactatg cttatgtagg cgcctctttt gttccttata    4980
tcaactgggc aattaaagat gcaattaaac gcggctatga aaccatttac tttatctctc    5040
gcgatgggca tttcttaaag caaattgcta caaaaattat tgaaattcgt ggctataacg    5100
taaaaacaaa atatatctac ggttcacgta agcatggcg tttaccttct ttcattacca     5160
aagttgatga tgaaaccttc tggcaatttg gtaactttgt cggtatggat agctttgaag    5220
atttggtgaa agccagttat ttaagcgaaa gtgaactctt atctctcttc cctgaatttg    5280
aaagtttacg tcatgccaaa caccttcgtg gtgaaatagc tgaaacatt cgtaaaattt     5340 tcaaaaattc acccgcttac catgagaaag tgttagcgat cgccgctgaa aaacgcaaaa    5400
tggtacgcca atacattcaa caagaaatta atccaaaaga aaatttgcg tttgttgaat     5460 tctgggggcg aggctataca caagatacct ttggtcgtct gctaaatgat gcctttggta    5520
```

```
aagaagtaaa aaacccattc tattatgtca gaagttttac tgatgatatg ggtacatctg    5580
ttcgccataa cttcatctta gcaccacaaa acttctcatt cttcgagcct attttttgcac   5640 aaacccata  cgacagtatt cctgattact acgaagaaaa aggcagaatt gaaccaatta    5700
ttaatcaccg agatagaagc gtaagcgatc tcatttcgga agggttatta aaatttacag    5760
aagattactt agcactcaat acgcaagacg aagattactt tgatgcagca ttatcgcaat    5820
ttaactatca atatcagtta aatacaccaa atgatcaatt tatttgcaat gtattcagtg    5880
aattaaaaga taacatttca gttttggtg  tagaaaaacc ttatgcacca gcattaacgc    5940
tgaaacagct tgaaagtatc acctctaaac aagagctgga taaactgact caatcaattc    6000
ctatctcact ctcaaaaagt gatgtaaaag taattgatta ttataataaa attcagaaaa    6060
actataattt accggcatat aacagcacac caatgcgtaa agcttatgca gtaaacccat    6120
tagaacaata tgtttggagc acacaggttc catttagagt actttcatta aaacaaaaca    6180
gcttctattt agatgtgagt tttgctgaaa cgaccaaacg aaaagatatt ttcttaaaag    6240
aattaaatga aatcgatgtt attgccgttg attggttaaa aggcggggtt ccgcgtttat    6300
taacagagca cggatatatt acggctcata agactgggt  aaaaaaatca tttaatgatg    6360
ataaaaccaa taatattgaa gaacctaagg taaaaaataa agagaaaagt aaggtactag    6420
aagtaaatac tactgtaacc aataacaata acaagctat  tggtaagtta gataataata    6480
ttgataagtc aaataaagag cagaagaaac gtaagctagc tagaaatcct tatgcttttt    6540
tcaatgattc taaaaaacct atattaaata gtcttaagca tttatttaat gagagccatt    6600
ccttaggcag acttctaagt aggattgtta gaaaaacact taaccatgat aataatcag    6660 gacaattaaa tgaatattaa aaatatagca attaacttt  catctaaaaa agattttcta    6720
aataattttg gtaaaattaa taatgaaaaa acgagcttat ccataataaa taaaaacgag    6780
attattataa aaggtaaaaa aaatgataat tctcttaact ttactttatt aaaaaataaa    6840
aaatatttaa aacctgggaa gacttatact atttcctgtg attttattct taataaaaaa    6900
atatctaaaa cattaccttt tgatgttcct aaaattgctt ttgattgtac aattaatgga    6960
aaagataact ttgactatca atctagctca tctattccta atgaagtggg agtttggcat    7020
aaatctttga ccgtcaaagt tcctaaaaat tgttctaatg catggtttag aatttatgtg    7080
ggaatagaaa aagatgctgg cgaattatta ataaaaaata tttttatatc agagaataac    7140
tttgatttca tttacttaaa taatctattc tatcacaatg aagataatga acttttttct    7200
ttattatctg atttcaaaga aaactatatt gaaaaatgta atgatgtatc ttatctcttt    7260
agaaatggac actacacatt cgtcaactca atcattaaaa atattaatga tagtgcaata    7320
agaaaaaaat ttaagttata tttagttatg tcaaaagaaa atgtatcggg tacattagct    7380
tactttaaca atattaaaaa tgaacttaac gagcaagatt ctgttttagc ttctgacgca    7440
atacattttt ttgctagaaa tttaaaatgg acacaatta  aagatatagt aaatttttc    7500 gataaaaag  gattgtacca caactgcata gaatatttat atgagaaggc tcagctttat    7560
agaagattaa aagataaaga aaatgaatta aaatactata atcttgcatt atccatagat    7620
gaaaataaaa atccaaatat aaattggaat ctattttttg atagtaataa tccaggtcta    7680
agctatagaa gagatgaatt aaagtttatt ctagaaaact tatcagacat acagagaatt    7740
gccgattcct atccttcttc tcatatcaac tttaaagaat cgccagtttt tgtcttttgg    7800
gatcaaggat atgataacgc gccgctcata gtaaaatcta tgatagacag aatgaaaata    7860
atatatggta ataaactggt atttcttact ggagaaacta tagaggctta tatagatata    7920
```

```
ccggctagaa tagaaagttt cagagaatct aaaagagcct ttttctcaga ttatattcgt    7980
acagaattat tattgagata tggtggtact tggatagatt caactgtatt cacaacgaat    8040
caattttata aagagaattt agaaatatta gaaaaaaatg ataataatct atatgtacta    8100
agaattcctg aaaatccata ccgaatttct aattggtttt tatcaacaaa ccaaactgga    8160
aatagaatac tggctttaat gtatgcaact atgttgattt ttgctgaaaa agaaacagt     8220 ctatttgaat attatcaata ccatacccttt tttgaaatct aacacagtt agataaacaa    8280 gctaatgaag actttcataa aaattataga ataactatc aaccttatgc acatgatgtg     8340
ttaaaaaact ttagaaatga ttgggataga gagttattta ataaactaat tgcttgctgt    8400
ccaatacaaa aactgacata taatctaat ttattacact taagaacaca ttctttttac     8460
aaaactatta ttagaaatgc agcttttta taaaagccaa tctaaacttt tacttaagca     8520
gtcatatttt catgattttt tcaaaatgct gaaaaacatg accgcacttt tacccaggat    8580
aactagaata aaatcaccat gccaactgca ctgattttct cgcacggaat caaaaaaatt    8640
```

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 80

```
gcgaaagtga actcttatct ctc                                              23
```

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 81

```
gcttacgctt ctatctcggt gaa                                              23
```

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 82

```
accatgagaa agtgttagcg                                                  20
```

<210> SEQ ID NO 83
<211> LENGTH: 273
<212> TYPE: DNA
<213> ORGANISM: Haemophilus parainfluenzae

<400> SEQUENCE: 83

```
acttttggcg gttactctgt tgaagatctt cagcaacgtt acaacaccgt ttacttccgt     60
ttcgacaaat tcaacatcga aggtgaatac gttcaaatct tagatgctca cgctgcatac    120
ttaaatgcaa ctccagcttc taaagttgtt gttgaaggta acactgacga acgtggtact    180
```

```
ccagagtaca acatcgcttt aggtcaacgt cgtgctgatg cagttaaagg tttcttaact    240
ggtaaaggtg ttgatgctgg taaattaggc aca                                 273
```